United States Patent
Nakauchi et al.

(10) Patent No.: US 7,150,990 B2
(45) Date of Patent: Dec. 19, 2006

(54) SELF-RENEWING PLURIPOTENT HEPATIC STEM CELLS

(75) Inventors: Hiromitsu Nakauchi, Ibaraki (JP); Atsushi Suzuki, Ibaraki (JP); Hideki Taniguchi, Ibaraki (JP); Katashi Fukao, Ibaraki (JP)

(73) Assignee: ReproCell, Inc., Tokyo (JP)

( * ) Notice: Subject to any disclaimer, the term of this patent is extended or adjusted under 35 U.S.C. 154(b) by 561 days.

(21) Appl. No.: 10/093,311

(22) Filed: Mar. 6, 2002

(65) Prior Publication Data

US 2003/0186439 A1    Oct. 2, 2003

(51) Int. Cl.
  C12N 5/06    (2006.01)
  C12N 5/10    (2006.01)
  A01N 63/00   (2006.01)
  C12N 5/08    (2006.01)

(52) U.S. Cl. ........................ 435/354; 435/325
(58) Field of Classification Search ............... 424/93.1; 435/325, 370, 377
See application file for complete search history.

(56) References Cited

OTHER PUBLICATIONS

Suzuki et al. Clonal identification and characterization of self-renewing pluripotent stem cells in the developing liver. J. Cell Biology 156:173-184, 2002.*
Suzuki et al. Identification and propagation of liver stem cells. Seminars in Cell & Developmental Biology 13:455-461, 2002.*
Sandhu et al. Stem cell properties and repopulation of the rat liver by fetal liver epithelial progenitor cells. Am. J. Pathology 159:1323-1334, 2001.*
Forbes et al. Hepatic stem cells. J. Pathology 197:510-518, 2002.*
Suzuki et al. Flow-cytometric separation and enrichment of hepatic progenitor cells in the developing mouse liver. Hepatology 32:1230-1239, 2000.*
Ema, H. et al., *J. Exp. Med.* 192(9):1281-1288, 2000.
Temple, S., *Nature* 340:471-473, 1989.
McDonald, J. et al., *Nature Medicine* 5(12):1410-1412, 1999.
Sandgren, E. et al., *Cell* 66:245-256, 1991.
Schmidt, C. et al., Nature 373:699-702, 1995.
Hynes, R., *Cell* 69:11-25, 1992.
Couvelard, A. et al., *Hepatology* 27:839-847, 1998.
Pittenger, M. et al., *Science* 284:143-147, 1999.
Spangrude, G. et al., *Science* 241:58-62, 1988.
Kusakabe, M. et al., *Cell Biology* 107:257-265, 1988.
Yoshiki, A. et al., *J. Histochem. And Cytochem.* 41(10):1583-1590, 1993.
Petersen, B. et al., *Science* 284:1168-1170, 1999.
Stamatoglou, S. et al., *J. Cell Biology* 116(6):1507-1515, 1992.
Volpes, R. et al., *American Journal of Pathology* 142(5):1483-1492, 1993.
Volpes, R. et al., *Gastroenterology* 101:200-206, 1991.
Petersen, B. et al., *Hepatology* 27(2):433-445, 1998.
Overturf, K. et al., *American Journal of Pathology* 151(5):1273-1280, 1997.
Taniguchi, H. et al., *Nature Medicine* 2(2):198-203, 1996.
Morrison, S. et al., *Cell* 96:737-749, 1999.
Crosby, H. et al., *Gastroenterology* 120:534-544, 2001.
Dabeva, M. et al., *American Journal of Pathology* 156(6):2017-2031, 2000.
Deutsch, G. et al., *Development* 128:871-881, 2001.
Jensen, J. et al., *Nature Genetics* 24:36-44, 2000.
Kaneko, S. et al., *Human Gene Therapy* 12:35-44, 2001.
Kubota, H. and Reid, L., *Proc. Natl. Acad. Sci. USA* 97(22):12132-12137, 2000.
Laconi, E. et al., *Amer. Journal of Pathology* 153(1):319-329, 1998.
Suzuki, A. et al., *Transplantation Proceedings* 32:2370-2371, 2000.
Overturf, K. et al., *Nature Genetics* 12:266-273, 1996.
Overturf, K. et al., *Amer. Journal of Pathology* 155(6):2135-2143, 1999.
Ory, D. et al., *Proc. Natl. Acad. Sci. USA* 93:11400-11406, 1996.
Zulewski, H. et al., *Diabetes* 50:521-533, 2001.
Shiojiri, N. et al., *Cancer Research* 51:2611-2620, 1991.

* cited by examiner

*Primary Examiner*—Quang Nguyen
(74) *Attorney, Agent, or Firm*—Perkins Coie LLP

(57) ABSTRACT

The present invention provides clonal pluripotent hepatic stem cells using flow cytometry and in vitro single-cell-based assays. These cells possess multilineage differentiation potential and self-renewing capability. These cells may be clonally propagated in culture, to continuously produce hepatocytes and cholangiocytes as descendants while maintaining primitive stem cells. When expanded cells are transplanted into recipient animals, they morphologically and functionally differentiated into hepatocytes and cholangiocytes, with reconstitution of hepatocyte and bile duct structures. Furthermore, these cells differentiated into pancreatic ductal and acinar cells or intestinal epithelial cells when transplanted into pancreas or duodenal wall. Thus, the self-renewing multipotent stem cells persist in the developing mouse liver and can be induced to become cells of other organs of endodermal origin under appropriate microenvironment, providing new insight into therapies for diseases of the digestive system.

4 Claims, 5 Drawing Sheets

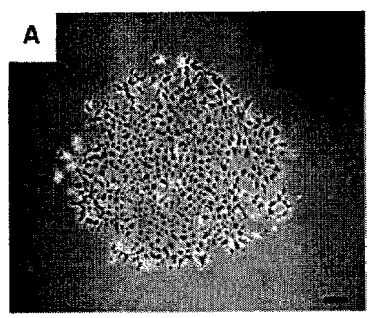
Fig. 2A
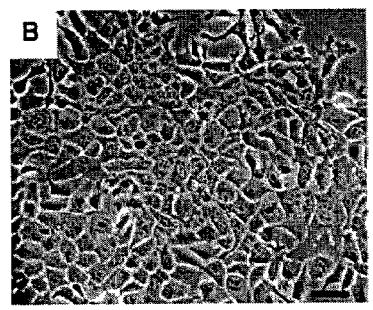
Fig. 2B
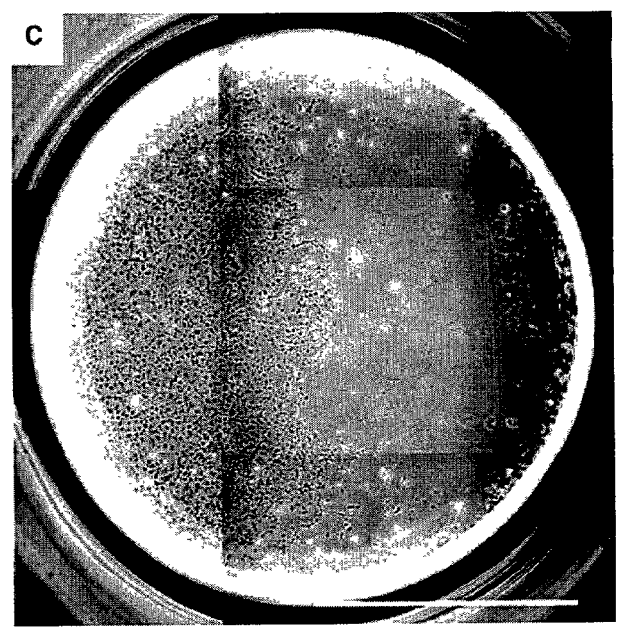
Fig. 2C
 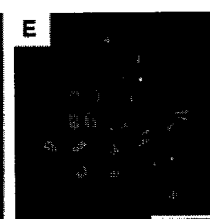 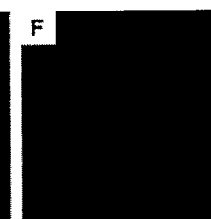 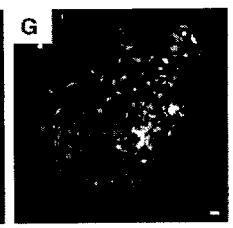
Fig. 2D  Fig. 2E  Fig. 2F  Fig. 2G
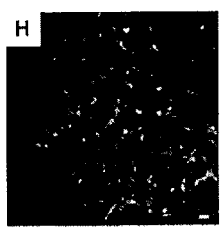 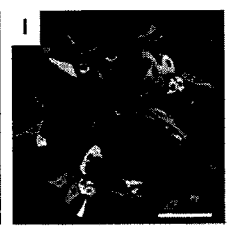  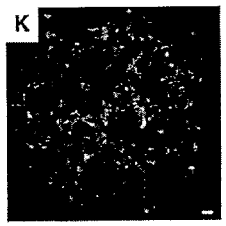 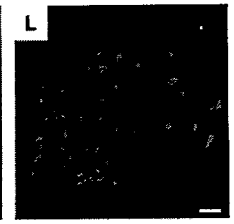
Fig. 2H  Fig. 2I  Fig. 2J  Fig. 2K  Fig. 2L
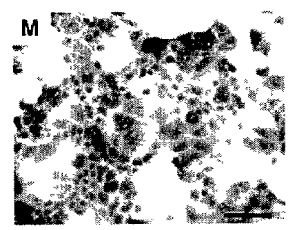 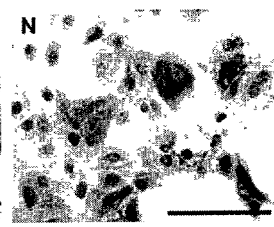
Fig. 2M     Fig. 2N

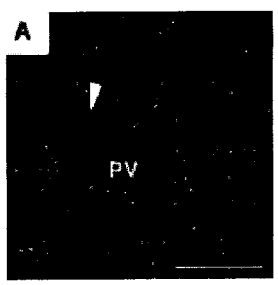 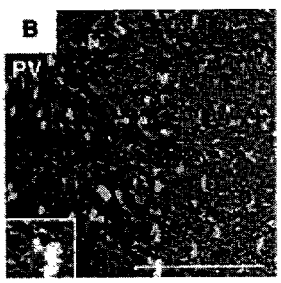
Fig. 5A   Fig. 5B
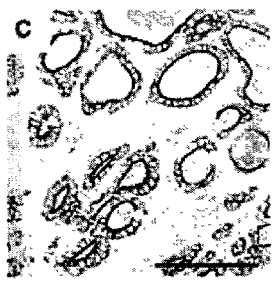 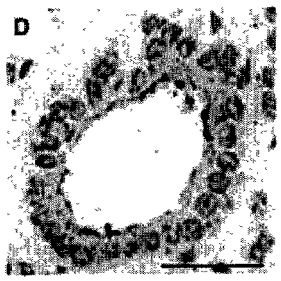
Fig. 5C   Fig. 5D
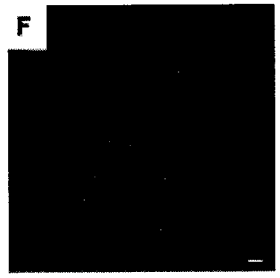 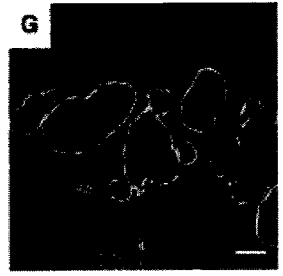
Fig. 5F   Fig. 5G
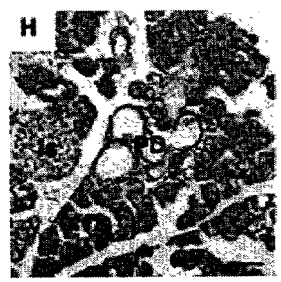 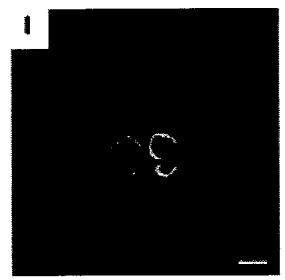
Fig. 5H   Fig. 5I
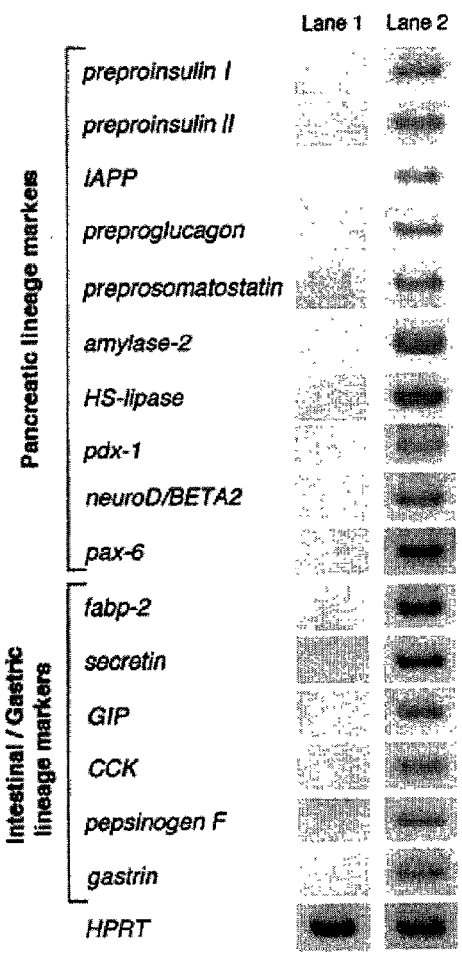
Fig. 5E
 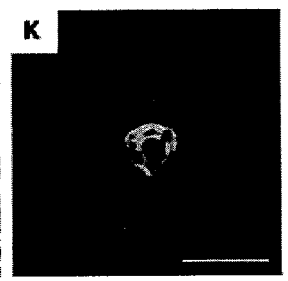 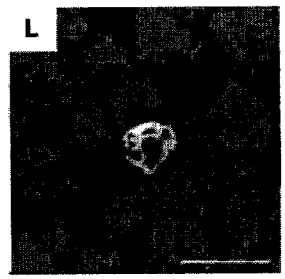 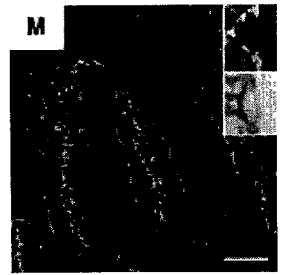
Fig. 5J   Fig. 5K   Fig. 5L   Fig. 5M

SEQUENCE LISTING

```
<160> NUMBER OF SEQ ID NOS: 48

<210> SEQ ID NO 1
<211> LENGTH: 19
<212> TYPE: DNA
<213> ORGANISM: Artificial Sequence
<220> FEATURE:
<223> OTHER INFORMATION: marker

<400> SEQUENCE: 1
tgtccagcgc aggcacttg                                                  19

<210> SEQ ID NO 2
<211> LENGTH: 20
<212> TYPE: DNA
<213> ORGANISM: Artificial Sequence
<220> FEATURE:
<223> OTHER INFORMATION: marker

<400> SEQUENCE: 2
caaagatgtc ctgcaggatg                                                 20

<210> SEQ ID NO 3
<211> LENGTH: 19
<212> TYPE: DNA
<213> ORGANISM: Artificial Sequence
<220> FEATURE:
<223> OTHER INFORMATION: marker

<400> SEQUENCE: 3
aagctggtct cagccacgg                                                  19

<210> SEQ ID NO 4
<211> LENGTH: 19
<212> TYPE: DNA
<213> ORGANISM: Artificial Sequence
<220> FEATURE:
<223> OTHER INFORMATION: marker

<400> SEQUENCE: 4
ctgaggtgaa gacctgctt                                                  19

<210> SEQ ID NO 5
<211> LENGTH: 19
<212> TYPE: DNA
<213> ORGANISM: Artificial Sequence
<220> FEATURE:
<223> OTHER INFORMATION: marker
```

<400> SEQUENCE: 5
gtcgcaagga cccctcagg                                    19

<210> SEQ ID NO 6
<211> LENGTH: 21
<212> TYPE: DNA
<213> ORGANISM: Artificial Sequence
<220> FEATURE:
<223> OTHER INFORMATION: marker

<400> SEQUENCE: 6
cttgaagtcc agcttgtgct g                                 21

<210> SEQ ID NO 7
<211> LENGTH: 20
<212> TYPE: DNA
<213> ORGANISM: Artificial Sequence
<220> FEATURE:
<223> OTHER INFORMATION: marker

<400> SEQUENCE: 7
cttctccgtg tcaggagcac                                   20

<210> SEQ ID NO 8
<211> LENGTH: 19
<212> TYPE: DNA
<213> ORGANISM: Artificial Sequence
<220> FEATURE:
<223> OTHER INFORMATION: marker

<400> SEQUENCE: 8
ctgggtagtg catgacctg                                    19

<210> SEQ ID NO 9
<211> LENGTH: 20
<212> TYPE: DNA
<213> ORGANISM: Artificial Sequence
<220> FEATURE:
<223> OTHER INFORMATION: marker

<400> SEQUENCE: 9
tctgccacca ctacagctgc                                   20

<210> SEQ ID NO 10
<211> LENGTH: 21
<212> TYPE: DNA
<213> ORGANISM: Artificial Sequence
<220> FEATURE:
<223> OTHER INFORMATION: marker

<400> SEQUENCE: 10
cgctgctagg atgcattaag c                                 21

<210> SEQ ID NO 11
<211> LENGTH: 20
<212> TYPE: DNA
<213> ORGANISM: Artificial Sequence
<220> FEATURE:
<223> OTHER INFORMATION: marker

<400> SEQUENCE: 11
cttccaagag ctgcagattg                                   20

<210> SEQ ID NO 12

```
<211> LENGTH: 20
<212> TYPE: DNA
<213> ORGANISM: Artificial Sequence
<220> FEATURE:
<223> OTHER INFORMATION: marker

<400> SEQUENCE: 12
cttgtaggat tcagatcccg                                                    20

<210> SEQ ID NO 13
<211> LENGTH: 21
<212> TYPE: DNA
<213> ORGANISM: Artificial Sequence
<220> FEATURE:
<223> OTHER INFORMATION: marker

<400> SEQUENCE: 13
tggtatttgt gtctgaagct g                                                  21

<210> SEQ ID NO 14
<211> LENGTH: 21
<212> TYPE: DNA
<213> ORGANISM: Artificial Sequence
<220> FEATURE:
<223> OTHER INFORMATION: marker

<400> SEQUENCE: 14
ttaataagaa tgcttcacgg c                                                  21

<210> SEQ ID NO 15
<211> LENGTH: 21
<212> TYPE: DNA
<213> ORGANISM: Artificial Sequence
<220> FEATURE:
<223> OTHER INFORMATION: marker

<400> SEQUENCE: 15
tgcgcaagaa cttcagagtg a                                                  21

<210> SEQ ID NO 16
<211> LENGTH: 21
<212> TYPE: DNA
<213> ORGANISM: Artificial Sequence
<220> FEATURE:
<223> OTHER INFORMATION: marker

<400> SEQUENCE: 16
agcaacagct cattgtagtc t                                                  21

<210> SEQ ID NO 17
<211> LENGTH: 21
<212> TYPE: DNA
<213> ORGANISM: Artificial Sequence
<220> FEATURE:
<223> OTHER INFORMATION: marker

<400> SEQUENCE: 17
aagtgatggg agtctgatgt t                                                  21

<210> SEQ ID NO 18
<211> LENGTH: 21
<212> TYPE: DNA
<213> ORGANISM: Artificial Sequence
<220> FEATURE:
<223> OTHER INFORMATION: marker

<400> SEQUENCE: 18
```
ttctttgctg actcaacaca t                          21

<210> SEQ ID NO 19
<211> LENGTH: 21
<212> TYPE: DNA
<213> ORGANISM: Artificial Sequence
<220> FEATURE:
<223> OTHER INFORMATION: marker

<400> SEQUENCE: 19
agttacctga gtggaacttt g                          21

<210> SEQ ID NO 20
<211> LENGTH: 21
<212> TYPE: DNA
<213> ORGANISM: Artificial Sequence
<220> FEATURE:
<223> OTHER INFORMATION: marker

<400> SEQUENCE: 20
ttcgcacacc cgatgcaaga t                          21

<210> SEQ ID NO 21
<211> LENGTH: 21
<212> TYPE: DNA
<213> ORGANISM: Artificial Sequence
<220> FEATURE:
<223> OTHER INFORMATION: marker

<400> SEQUENCE: 21
cccaagacgt aacagcttct g                          21

<210> SEQ ID NO 22
<211> LENGTH: 21
<212> TYPE: DNA
<213> ORGANISM: Artificial Sequence
<220> FEATURE:
<223> OTHER INFORMATION: marker

<400> SEQUENCE: 22
cagtctcgta catgaccaca g                          21

<210> SEQ ID NO 23
<211> LENGTH: 22
<212> TYPE: DNA
<213> ORGANISM: Artificial Sequence
<220> FEATURE:
<223> OTHER INFORMATION: marker

<400> SEQUENCE: 23
tcctgatgaa ccgtcgcagt tg                         22

<210> SEQ ID NO 24
<211> LENGTH: 21
<212> TYPE: DNA
<213> ORGANISM: Artificial Sequence
<220> FEATURE:
<223> OTHER INFORMATION: marker

<400> SEQUENCE: 24
tgtcagccac cacatgttgt c                          21

<210> SEQ ID NO 25
<211> LENGTH: 20
<212> TYPE: DNA

```
<213> ORGANISM: Artificial Sequence
<220> FEATURE:
<223> OTHER INFORMATION: marker

<400> SEQUENCE: 25
agaaggtgac cagcctgaca                                                   20

<210> SEQ ID NO 26
<211> LENGTH: 20
<212> TYPE: DNA
<213> ORGANISM: Artificial Sequence
<220> FEATURE:
<223> OTHER INFORMATION: marker

<400> SEQUENCE: 26
aatgaagtcc agggcttgga                                                   20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ctgttggtgc acttcctacc                                                   20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gcagtagttc tccagctggt                                                   20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
tcaagcagca cctttgtggt t                                                 21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gttgcagtag ttctccagct g                                                 21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
tgtcctcctc atcctctctg t                                                 21
```

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tatgtattcg atcccacgtt g                                      21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
atttactttg tggctggatt g                                      21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tgtcagtgat cttggtttga a                                      21

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
ctctgcatcg tcctggcttt                                        20

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
caggatgtga atgtcttcca g                                      21

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
agtacctgtg gaagttacct                                        20

<210> SEQ ID NO 38
<211> LENGTH: 20
<212> TYPE: DNA
<213> ORGANISM: Artificial Sequence
<220> FEATURE:

```
<223> OTHER INFORMATION: primer

<400> SEQUENCE: 38
acacaagggc tctgtcagaa                                                      20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
tcttcttcga gggtgatgaa                                                      20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
taccttgctg tcctgtcctt                                                      20

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
ttacaagctc gctgggatca c                                                    21

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
aggtcaccgc acaatcttgc t                                                    21

<210> SEQ ID NO 43
<211> LENGTH: 21
<212> TYPE: DNA
<213> ORGANISM: Artificial Sequence
<220> FEATURE:
<223> OTHER INFORMATION: marker

<400> SEQUENCE: 43
attcgacggc acgtggaaag t                                                    21

<210> SEQ ID NO 44
<211> LENGTH: 21
<212> TYPE: DNA
<213> ORGANISM: Artificial Sequence
<220> FEATURE:
<223> OTHER INFORMATION: marker

<400> SEQUENCE: 44
aagaatcgct tggcctcaac t                                                    21
```

-continued

```
<210> SEQ ID NO 45
<211> LENGTH: 20
<212> TYPE: DNA
<213> ORGANISM: Artificial Sequence
<220> FEATURE:
<223> OTHER INFORMATION: marker

<400> SEQUENCE: 45
aagacactca gacggaatgt                                              20

<210> SEQ ID NO 46
<211> LENGTH: 20
<212> TYPE: DNA
<213> ORGANISM: Artificial Sequence
<220> FEATURE:
<223> OTHER INFORMATION: marker

<400> SEQUENCE: 46
tggttgtttc agtccactct                                              20

<210> SEQ ID NO 47
<211> LENGTH: 21
<212> TYPE: DNA
<213> ORGANISM: Artificial Sequence
<220> FEATURE:
<223> OTHER INFORMATION: marker

<400> SEQUENCE: 47
acctagacct ggtctacatt g                                            21

<210> SEQ ID NO 48
<211> LENGTH: 21
<212> TYPE: DNA
<213> ORGANISM: Artificial Sequence
<220> FEATURE:
<223> OTHER INFORMATION: marker

<400> SEQUENCE: 48
agtgaagctc tccatggtag t                                            21
```

SELF-RENEWING PLURIPOTENT HEPATIC STEM CELLS

BACKGROUND OF THE INVENTION

1. Field of the Invention

The present invention relates to stem cells. More specifically, the present invention relates to self-renewing pluripotent hepatic stem cells.

2. Description of the Related Art

The enormous regenerative capacity of the liver after partial hepatectomy or chemical injury is well known. In rodents, liver weight returns to normal within a few weeks even after loss of up to two-thirds of total liver mass (Fausto, N., and E. M. Webber. 1994. Liver regeneration: *The liver*. I. M. Arias, J. L. Boyer, N. Fausto, W. B. Jakoby, D. A. Schachter, and D. A. Shafritz, editors: Raven Press, N.Y., ed. 3, 1059–1084.). Remarkable regenerative potential is also retained in hematopoiesis. Hematopoietic stem cells(HSCs) certainly exist in bone marrow where they self-renew and differentiate along all hematopoietic lineages. Sophisticated isolation methods have recently identified a highly probable HSC candidate; a single such cell can reconstitute bone marrow (Osawa, M., K. Hanada, H. Hamada, and H. Nakauchi. 1996. Long-term lymphohematopoietic reconstitution by a single CD34-low/negative hematopoietic stem cell. *Science* 273: 242–245). By analogy with hematopoiesis, liver regeneration can be regarded as mediated by proliferation and differentiation of hepatic stem cells. However, it remains unclear how the liver is regenerated and what cells are involved in such regeneration. Overturf et al. (1997) inferred from serial transplantation studies the presence in adult mouse liver of cells capable of dividing more than 60 times; they ascribed this great reconstitutive ability to hepatic stem/progenitor cells (Overturf, K., M Al-Dhalimy, C. N. Ou, M. Finegold, and M. Grompe. 1997. Serial transplantation reveals the stem-cell-like regenerative potential of adult mouse hepatocytes. *Am. J. Pathol.* 151: 1273–1280). However, examination in greater detail strongly indicated that fully differentiated hepatocytes but not progenitors divided intensively after cell transplantation. In addition, the reconstitutive capacity of serially transplanted hepatocytes was as high as that of freshly isolated hepatocytes (Overturf, K., M. Al-Dhalimy, M. Finegold, and M. Grompe. 1999. The repopulation potential of hepatocyte populations differing in size and prior mitotic expansion. *Am. J. Pathol.* 155: 2135–2143). Of major importance in understanding proliferative processes in the liver is to recognize that fully differentiated hepatocytes themselves possess great growth potential and that stem cells may not be required for liver regeneration (Michalopoulos, G. K., and M. C. DeFrances. 997. Liver regeneration. *Science* 276: 60–66).

By contrast, it is believed that in the developing liver both hepatocytes and cholangiocytes differentiate from a common cell component, the hepatoblast (Shiojiri, N. 1984. The origin of intrahepatic bile duct cells in the mouse. *J. Embryol. Exp. Morphol.* 79: 25–39; Shiojiri, N., J. M. Lemire, and N. Fausto. 1991. Cell lineages and oval cell progenitors in rat liver development Cancer Res. 51: 2611–2620; and Fausto, N. 1994. Liver stem cells: The liver. I. M. Arias, J. L. Boyer, N. Fausto, W. B. Jakoby, D. A. Schachter, and D. A. Shafritz, editors: Raven Press, N.Y., ed. 3. 1501–1518). It was reported that fetal rat liver cells transplanted into retrorsine-treated liver reconstituted bile duct and hepatocyte structures (Dabeva, M. D., P. M. Petkov, J. Sandhu, R. Oren, E. Laconi, E. Hurston, and D. A. Shafritz. 2000. Proliferation and differentiation of fetal liver epithelial progenitor cells after transplantation into adult rat liver. *Am. J. Pathol.* 156: 2017–2031).This result suggested that the donor cell population included at least bipotent hepatic stem/progenitor cells. However, it was not possible to determine if the regenerated structures had differentiated from stem cells or from lineage-committed cells. Recently, by combining FACS® and in vitro clonal analysis bipotent hepatic progenitor cells have been isolated from rats or mice (Kubota, H., and L. M. Reid. 2000. Clonogenic hepatoblasts, common precursors for hepatocytic and biliary lineages, are lacking classical major histocompatibility complex class I antigen. *Proc. Natl. Acad. Sci. USA* 97: 12132–12137; Suzuki, A., Y. Zheng, R. Kondo, M. Kusakabe, Y. Takada, K. Fukao, H. Nakauchi, and H. Taniguchi. 2000. Flow cytometric separation and enrichment of hepatic progenitor cells in the developing mouse liver. Hepatology 32: 1230–1239). Although these data demonstrated that isolated cell is a possible candidate for the hepatic stem cell in the developing liver, its self renewal potential and multiple differentiation capability remain largely unanswered. For this reason, isolated progenitor cells have never been identified as hepatic stem cells.

Stem cells are generally defined as clonogenic cells capable of both self-renewal and multilineage differentiation (Till, J. E., and E. A. McCulloch. 1961. A direct measurement of the radiation sensitivity of normal mouse bone marrow cells. Radiat. Res. 14: 1419–1430; Metcalf, D., and M. A. S. Moore. 1971. Hematopoietic Cells (Amsterdam. North-Holland)). During development and regeneration of a given tissue, such cells give rise to non self-renewing progenitors with restricted differentiation potential and finally to functionally mature cells. In the study reported here, using in vitro single cell-based assays, we further enriched candidate hepatic stem cells and clonogenically identified cells with self-renewing capability and multilineage differentiation potential. These cells could be clonally propagated in culture for >6 months where they continuously produced hepatocytes and cholangiocytes as descendants. The value of stem cells expanded in vitro is expected to be great not only in conventional studies of their differentiation or self-renewing potential but also in therapy, for example, with virus-mediated gene transfer or as theoretically unlimited sources of cells Furthermore, upon cell transplantation these cells differentiated not only into hepato-biliary lineage cells but cells in other organs of endodermorigin such as pancreas and intestine. Thus, the stem cells that we isolated may actually be primitive endodermalstem cells persisting in fetal mouse liver. Alternatively, these findings may reflect lineage plasticity or transdifferentiation of hepatic stem cells.

We have previously reported that cells in ED 13.5 fetal mouse liver cells which co-express CD49f and CD29 ($\alpha 6$ and $\beta 1$ integrin subunits) but do not express c-Kit (stem cell factor receptor), CD45 (leukocyte common antigen), or TER119 (a molecule resembling glycophorin and exclusively expressed on immature erythroid cells) are the best candidate hepatic stem/progenitor cells (Suzuki et al., 2000).

Previously, there have been no cloned hepatic stem cells reported which are capable of renewing and multiply differentiating into a variety of cells. Therefore, there remains need for providing such cloned hepatic stem cells which are capable of self-renewing and possesse pluripotency, e, g., for use in the regenerative therapy, particularly for treating liver diseases and disorders.

The object of the present invention is thus to provide such self-renewing and pluripotent cells.

SUMMARY OF THE INVENTION

The present invention provides, for the first time, clonal pluripotent hepatic stem cells. These cells have been obtained using flow cytometry and in vitro single-cell-based assays. These cells possess multilineage differentiation potential and self-renewing capability. These cells could be clonally propagated in culture, where they continuously produced hepatocytes and cholangiocytes as descendants while maintaining primitive stem cells. When cells that expanded in vitro were transplanted into recipient animals, they morphologically and functionally differentiated into hepatocytes and cholangiocytes, with reconstitution of hepatocyte and bile duct structures. Furthermore these cells differentiated Into pancreatic ductal and acinar cells or intestinal epithelial cells when transplanted into pancreas or duodenal wall. These data indicate that self-renewing multipotent stem cells persist in the developing mouse liver and that such cells can be induced to become cells of other organs of endodermal origin under appropriate microenvironment. Manipulation of hepatic stem cells may provide new insight into therapies for diseases of the digestive system.

In accordance with the forgoing objects, the invention includes the isolation, clonal expansion and differentiation of pluripotent hepatic stem cells such as those derived from the liver. The methods employ novel separation and culturing regimens and bioassays for establishing the generation of pluripotent hepatic stem cells and their derivatives.

These methods result in the production of non-transformed hepatic stem cells and their progeny. The invention demonstrates, for the first time at the clonal level, the self regeneration and asymmetrical division of hepatic stem cells.

Particularly, the method of the present invention comprises the following steps: providing cells from animal; and fractionating said cells by selecting cells expressing c-Met$^+$ CD49f$^{+/low}$.

The invention further includes transplantation assays which allow for the identification of pluripotent hepatic stem cells from various tissues. It also includes methods for transplanting hepatic stem cells and/or progeny thereof into a subject or a patient (such as mammal including primate, preferably human).

The invention also provides methods for obtaining a cellular composition from tissue or organ comprising one or more cells having at least one property characteristic of a pluripotent hepatic stem cell or a progeny of such cells The method comprises preparing a suspension comprising a population of cells from a tissue: selecting a pluripotent hepatic stem cell from the cell suspension having at least cellular markers characteristic of a pluripotent hepatic stem cell, and optionally proliferating said pluripotent hepatic stem cell.

The method comprises preparing a suspension comprising cells from a tissue; contacting the suspension with an antibody capable of forming a complex with a stem cell-specific surface marker on a pluripotent hepatic stem cells; and isolating the complex, if formed, to obtain said cellular composition.

The invention is also directed to cells made according to any of the foregoing methods.

The invention also includes cultures of genetically-engineered pluripotent hepatic stem cells Nucleic acid sequences encoding genes of interest are introduced into pluripotent hepatic stem cells where they are expressed.

These genes can include hepatotrophic or survival factors and immortalizing oncogenes. In addition, marker genes, such as the E. coli β-galactosidase gene, can be introduced to provide hepatic stem cells and their progeny which can be identified based on the expression of the marker gene. Selectable marker genes, such as the neomycin phosphoribosyltransferase (neomycin-resistance, neo$^r$) or hisD genes, may be introduced to provide for a population of genetically-engineered stem cells which are identified by the ability to grow in the presence of selective pressure (i.e., medium containing neomycin or L-histidinol). Hepatic stem cells may be transfected (genetically-engineered) with both a selectable marker and a non-selectable marker to provide hepatic stem cells which express both gene products.

The invention also includes methods for producing cultures of genetically-engineered mammalian pluripotent hepatic stem cells and their progeny.

Still further, the invention includes methods for immortalizing such cell lines by transfecting a hepatic progenitor cell or pluripotent stem cell precursor thereof with a vector comprising at least one immortalizing gene.

Further, the invention includes monoclonal antibodies capable of recognizing surface markers characteristic of mammalian pluripotent hepatic stem cells and their progeny. The invention also includes a method for screening hybridoma producing such monoclonal antibodies which comprises contacting live hepatic cells with monoclonal antibodies from a hybridoma and detecting whether the monoclonal antibody binds to the hepatic cell.

In addition to the foregoing, the invention includes methods for assaying the effects of substances on hepatic stem cells, Such methods comprise contacting a culture of at least one hepatic stem cell with a substance and determining the effect, if any, of the substance on the differentiation of the hepatic stem cell. Such differentiation can be to any cells related to the liver.

The invention also includes methods for producing a liver comprising culturing at least one hepatic stem cell under conditions which permit differentiation to a hepatocyte and bile duct structures. Such conditions can result in a heterogeneous population which includes hepatocytes and cholangiocytes. In alternate embodiments, factors instructive for hepatocyte differentiation are used which result in the preferential differentiation to hepatocyte at the expense of other cell lineages. Furthermore, the cells of the present invention can be differentiated into pancreatic ductal and acinar cells or intestinal epithelial cells when transplanted into pancreas or duodenal wall.

The stem cells of the present invention were deposited as FRCC Deposit No. Ferm BP-8116 on Jul. 12, 2002. The FRCC number referred to above is directed to a biological deposit with the FRCC, AIST Tsukuba Central 6, 1—1, Higashi 1-Chome Tsukuba-shi, Ibaraki-ken, 305-8566, Japan. The strain is being maintained under the terms of the Budapest Treaty and will be made available to a patent office signatory to the Budapest Treaty.

Thus, the invention described herein makes possible the advantages of (1) providing a clonal, self-renewing pluripotent hepatic stem cells; thereby (2) a clonal study of self-renewing pluripotent hepatic stem cells; and (3) treatment of hepatic diseases or disorders and/or conditions related to hepatic stem cell disorders.

These and other advantages of the present invention will become apparent to those skilled in the art upon reading and understanding the following detailed description with reference to the accompanying figures.

BRIEF DESCRIPTION OF THE DRAWINGS

FIG. 2. In vitro multilineage colony formation from a sorted c-Met⁺ CD49f$^{+/low}$ c-Kit⁻ CD45⁻ TER119⁻ cell. (A-B) Single cell culture of c-Met⁺ CD49f$^{+/low}$ c-Kit⁻ CD45⁻ TER119⁻ cells was performed on laminin-coated 96-well plates for 5 days, then H-CFU-C colonies were determined. (C) Some H-CFU-C formed even larger colonies when cultured for 21 days. Immunocytochemical staining was conducted after 5 days (D-G) or 21 days (H-L) of culture. Cells stained green for single-positive cells marking for albumin or red for cytokeratin 19. After 5 days of culture, most small colonies were composed of cells positive for only albumin (D) or cytokeratin19(E). Although most H-CFU-C colonies were formed by cells expressing neither marker (F), some of them included both cells expressing one marker and cells expressing the other (G). After 21 days of culture, most H-CFU-C colonies included both cells expressing albumin and cells expressing cytokeratin19(H-J), whereas a few of them were composed of cells that marked only for albumin (K) or for cytokeratin19(L). We also observed cells expressing both markers at once (shown in yellow, I, arrowhead). I and J are magnified pictures of the regions surrounded by broken lines in H and I. (M-N) PAS staining revealed that most H-CFU-C gave rise to functionally mature hepatocytes, containing abundant glycogen stores, following 21 days of culture, Scale bar: (A, D-N) 100 μm, (B) 50 μm, and (C) 2.5 mm.

FIG. 5. Clonally expanding H-CFU-C in culture reconstituted liver, pancreas, and intestine in vivo. (A-D) Thirty-eight days after transplantation of EGFP-tagged H-CFU-C, both livers and spleens were fixed and sectioned. (A) Many EGFP-positive donor cells are seen engrafted in hepatic cords of periportal zones, but not in bile ducts (arrowhead). (B) Overlay image of EGFP, phase-picture, and serial section stained by albumin (shown in red) clearly shows that many, but not all, EGFP-positive donor cells had differentiated into albumin-positive hepatocytes (shown in yellow). A detail is shown at higher magnification in the inset. (C) In the spleens of recipient mice, many bile duct-like structures were formed by keratin-positive donor-derived cholangiocytes. (D) Alcian blue staining (pH 2.5) (Mowry, 1963) also showed that the component cells contained abundant mucin near luminal membranes (counterstain, nuclear fast red). (E) Pancreatic, intestinal, and gastric marker expression were not detected in the sorted c-Met⁺ CD49f$^{+/low}$ c-Kit⁻ CD45⁻ TER119⁻ cells (lane 1). However, they became detectable in the progeny of a single H-CFU-C following several months of culture (lane 2). (F-G) A H-CFU-C clone isolated from EGFP transgenic fetal mice differentiated into (F) hepatocytes (6 months post-transplant) or (G) cholangiocytes (2 months) in recipient livers following either carbon tetrachloride or DAPM treatment. (H-M) Differentiation was also seen in cells constituting pancreas (4 months) and duodenum (2 months); (H-I) pancreatic ducts, (J-L) amylase-positive acinar cells (L, shown in yellow), (M) intestinal vili and crypts. Insets in M show EGFP-positive goblet cells stained in alcian blue. (H, J) hematoxylin/eosin stain. PV: portal venule. PD: pancreatic duct. Is: islet. Scale bar: (A, F-G, M) 100 μm, (B-C, H-L) 50 μm, and (D) 2.5 μm.

Figure 1A:
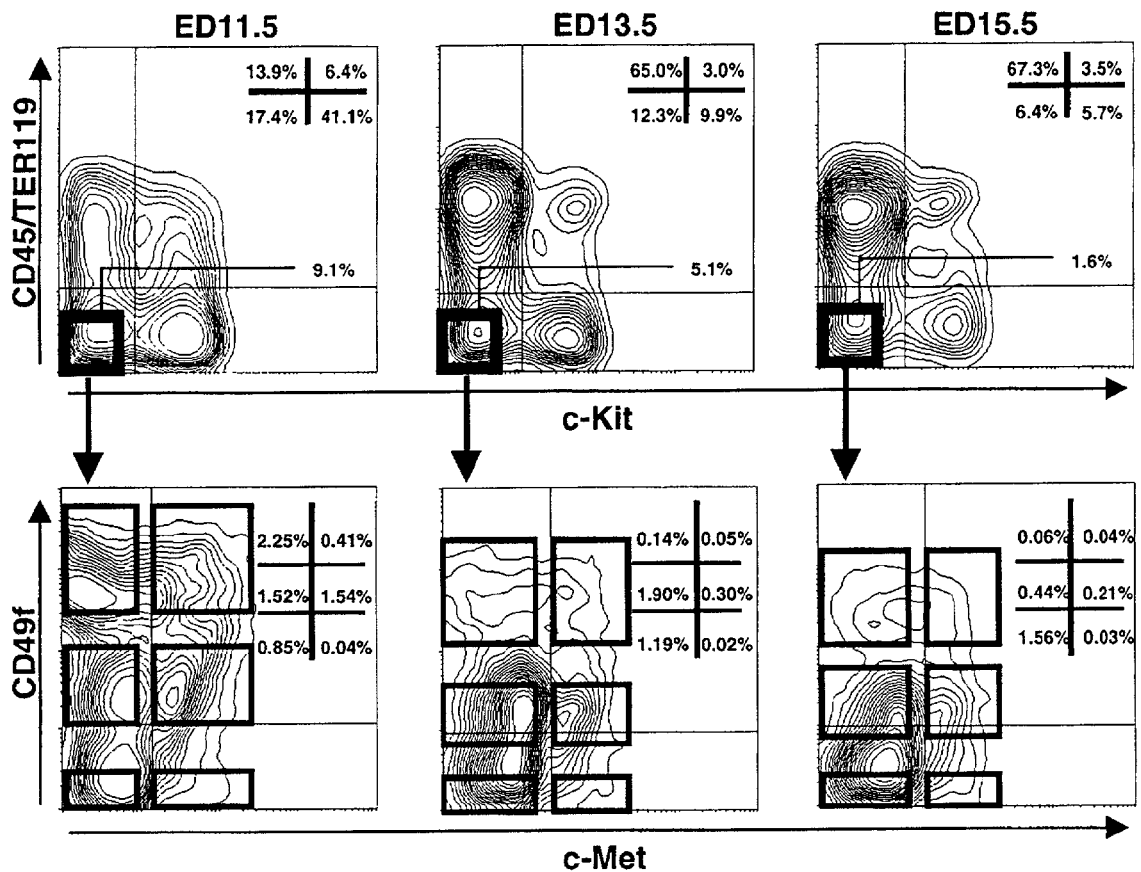
FIG. 1. Flow cytometric analysis of fetal mouse liver cells. (A) c-Kit⁻ CD45⁻ TER119⁻ cells among ED 11.5, ED 13.5, and ED 15.5 fetal mouse liver cells were fractionated by c-Met and CD49f expression. Sorting gates were then set for c-Met⁻ CD49f⁻, c-Met⁻ CD49f$^{+/low}$, c-Met⁻ CD49f$^{+/high}$, c-Met⁺ CD49f⁻, c-Met⁺CD49f$^{+/low}$, and c-Met⁺ CD49f$^{+/high}$ subpopulations. The percentage of fractionated cells is shown at upper right. Representative data from 6 independent experiments are shown. (B) Numbers of H-CFU-C per $3 \times 10^2$ cells in each cell subpopulation derived from ED 11.5, ED 13.5, and ED 15.5 fetal mouse livers. This graph shows the average of 18 dishes for each cell subpopulation in 6 independent experiments (n=6). (*; P<0.01, * *; P<0.005, * * * ; P<0.01)

DESCRIPTION OF THE PREFERRED EMBODIMENTS (i) Definitions

Unless specifically stated, the terms used in the specification have the same meaning as used in the art. For convenience, certain terms employed in the specification, examples, and appended claims are collected here.

As used herein the term "animal" refers to mammals, preferably mammals may be primates, such as humans. Likewise, a "patient" or "subject" to be treated by the method of the invention can mean either a human or non-human animal.

As used herein, the term "cellular composition" refers to a preparation of cells, which preparation may include, in addition to the cells, non-cellular components such as cell culture media, e. g. proteins, amino acids, nucleic acids, nucleotides, co-enzyme, anti-oxidants, metals and the like Furthermore, the cellular composition can have components which do not affect the growth or viability of the cellular component, but which are used to provide the cells in a particular format, e. g., as polymeric matrix for encapsulation or a pharmaceutical preparation.

The term "culture medium" is recognized in the art, and refers generally to any substance or preparation used for the cultivation of living cells. Accordingly, a "tissue culture" refers to the maintenance or growth of tissue, e. g., explants of organ primordia or of an adult organ in vitro so as to preserve its architecture and function. A "cell culture" refers to a growth of cells in vitro; although the cells proliferate they do not organize into tissue per se.

Tissue and cell culture preparations of the subject microorgan explants and amplified progenitor cell populations can take on a variety of formats. For instance, a "suspension culture" refers to a culture in which cells multiply while suspended in a suitable medium. Likewise, a "continuous flow culture" refers to the cultivation of cells or ductal explants in a continuous flow of fresh medium to maintain cell growth, e. g. viability. The term "unconditioned media" refers to the supernatant, e. g. free of the cultured cells/tissue, resulting after a period of time in contact with the cultured cells such that the media has been altered to include certain paracrine and/or autocrine factors produced by the cells and secreted Into the culture.

"Differentiation" in the present context refers to a status of cells in which the cells develop specific morphological or functional properties. Cells may "differentiate" into a specific tissue or organ. On the other hand, undifferentiated cells are difficult to distinguish each other in a population of cells, since each cell does not have any or little specific morphological or functional properties.

In the context of hepatic cells, "differentiation" refers to develop at least one property of the liver, including but not limited to:

1. Regulation of blood sugar: The level of blood sugar stays at around 0.1%, and excess coming from the gut is stored as glycogen. The hormone called insulin—excreted by the pancreas—causes the excess glucose to turn into glycogen.
2. Regulation of lipids: Lipids are extracted from the blood and changed to carbohydrates, etc. as required or sent to fat storage sites if not needed straight away.
3. Regulation of amino acids: a supply of amino acids in the blood is kept at a normal level. Any spare which has not been absorbed cannot be stored but is converted into the waste products, called urea when at the liver, and is then sent to the kidneys to be removed from the body as urine. The remainder of the amino acid molecule is not wasted; It is changed into a carbohydrate that can be used.
4. Production of heat: the liver is one of the hardest working regions of the body and produces a lot of waste heat. This is carried round the body in the blood and warms less active regions.
5. Forms bile: bile consists of bile salts and the excretory bile pigments. It is important to speed up th digestion of lipids.
6. Forms cholesterol: this fatty substance is used in the cells. Excess amounts in the blood can cause the blood vessels to become blocked, leading to heart attacks, etc.
7. Removals of hormones, toxins, etc. The liver extracts many harmful materials from the blood and excretes them in the bile or from the kidneys.
8. Formation of red blood cells in the young embryo while it is developing in the womb.
9. Making heparin: this is a substance that prevents the blood from clotting as it travels through the blood system.
10. Removal of hemoglobin molecules: when red blood cells die, the hemoglobin is converted into bile pigments and the iron atoms are saved for future use.
11. Storage of blood: the liver can swell to hold huge amounts of blood which can be released into the circulation if the body suddenly needs more, e. g. if it is wounded.
12. Forms plasma proteins: the plasma proteins are used in blood clotting and in keeping the blood plasma constant. The main blood proteins include fibrinogen, prothrombin, albumens and globulins.
13. Storage of vitamins such as vitamin A and D. Vitamin A is also made in the liver from carotene, the orange-red pigment in plants. Vitamin B12 is also stored in the liver.

The term "$ED_{50}$" means the dose of a drug which produces 50% of its maximum response or effect.

An "effective amount" of, e. g., HGF, with respect to the subject method, refers to an amount of a HGF elevating agent which, when added to the subject hepatic cell cultures, brings about a change In the rate of cell proliferation and/or the state of differentiation of a cell.

The term "explant" refers to a portion of an organ taken from the body and grown in an artificial medium.

By "ex vivo" is meant cells that have been taken from a body, temporarily cultured in vitro, and returned to a body.

The term "lineage committed cell" refers to a progenitor cell that is no longer pluripotent but has been induced to differentiate into a specific cell type, e. g. , a pancreatic, cell.

The term "organ" refers to two or more adjacent layers of tissue, which layers of tissue maintain some form of cell-cell and/or cell-matrix interaction to form a microarchitecture.

The term "primary culture" denotes a mixed cell population of human pancreatic cells that permits interaction of epithelial and mesenchymal cells within ICC. The word "primary" takes its usual meaning in the art of tissue culture.

The term "progenitor cell" refers to an undifferentiated cell which is capable of proliferation and giving rise to more progenitor cells having the ability to generate a large number of mother cells that can in turn give rise to differentiated, or differentiable daughter cells As used herein, the term "progenitor cell" is also intended to encompass a cell which is sometimes referred to in the art as a "stem cell". In a preferred embodiment, the term "progenitor cell" refers to a generalized mother cell whose descendants (progeny) specialize, often in different directions, by differentiation, e. g., by acquiring completely individual characters, as occurs in progressive diversification of embryonic cells and tissues. "Progenitor cells" refers to progenitor cells arising in tissue of a pancreatic intralobular duct and giving rise to such differentiated progeny as, for example, B cell lineages.

The term "proliferation" indicates an increase in cell number.

The term "tissue" refers to a group or layer of similarly specialized cells which together perform certain special functions.

The term "transplantation" refers to a process where a cell, a tissue or an organ is removed from a donor or otherwise prepared from non-host source such as using genetic engineering techniques and implanted into a patient or recipient. The recipient may receive a cell, a tissue or an organ from a living-related donors (syngenic transplantation) or the recipient per se. The most compatible match is usually a sibling, as their genetic make-up may closely match. The transplantation may be syngeneic, allogeneic or xenogeneic, When allogeneic or xenogeneic transplantation is conducted, rejection response may optionally obviated by any method known in the art such as administering immunosuppressive agent (e. g. azathiopurine, cyclophosphamide etc.).

The term "liver" is art recognized, and refers generally to a largest gland in the body, and is situated slightly below the diaphragm and anterior to the stomach. It consists of two lobes which are wedge-shaped. Two blood vessels enter the liver, namely the hepatic portal vein with dissolved food substances from the small intestine, and the hepatic artery, with oxygenated blood from the lungs. Two ducts originate in the liver, and these unite to form the common hepatic duct which opens, with the pancreatic duct, in the hollow side of the duodenum (the first section of the small intestine). The gall bladder lies inside the liver, and is the storage place for bile, which is formed by the liver cells.

The term "substantially pure", with respect to progenitor cells, refers to a population of progenitor cells that is at least about 75%, preferably at least about 85%, more preferably at least about 90%, and most preferably at least about 95% pure, with respect to progenitor cells making up a total cell population. Recast, the term "substantially pure" refers to a population of progenitor cell of the present invention that contain fewer than about 20%, more preferably fewer than about 10%, most preferably fewer than about 5%, of lineage committed cells in the original unamplified and isolated population prior to subsequent culturing and amplification.

(ii. Detailed Description of Preferred Embodiments of the Present Invention)

In one aspect, the invention provides a cloned, self-renewing pluripotent hepatic stem cell, or progeny thereof. Previously, self-renewing pluripotent hepatic stem cell was identified in a cell population having c-Kit$^-$ CD45$^-$ TER119$^-$. However, this cell population was not sufficient for clonal analysis or clinical application.

In a preferable embodiment of the present invention, a cloned, self-renewing pluripotent hepatic stem cell may be obtained by fractionating cells by selecting cells expressing c-Met$^+$ CD49f$^{+/low}$. Cells can be any cells, but preferably, fetal liver cells. The cells may be fractionated by selecting cells expressing c-Kit$^-$ CD45$^-$ TER119$^-$, which may be performed prior to or after the c-Met$^+$ CD49f$^{+/low}$ selection.

The inventive cells may be of any origin, preferably mammalian cells, including primate, rodent etc., and most preferably human cells.

In one embodiment, the inventive cell are capable of differentiating into hepatocytes or cholangiocytes.

In another embodiment, the inventive cell are capable of differentiating into pancreatic ductal, cinar or intestinal epithelial cells.

In another aspect of the invention, a purified composition essentially consisting of cloned, self-renewing pluripotent hepatic stem cells is provided. The cells contained in the composition may be further characterized as above.

In other aspect of the invention, the present invention provides a method for producing a cloned, self-renewing pluripotent stem cells, comprising providing cells: and fractionating said cells selecting cells expressing c-Met$^+$ CD49f$^{+/low}$.

In one embodiment of the Invention, the present method is further characterized in that the step of fractionating further comprising selecting cells expressing c-Kit$^-$ CD45$^-$ TER119$^-$. Preferably, the cell is a liver cell. In a preferable embodiment the cell used for obtaining the present stem cells Is a fetal liver cell.

In a further aspect, the present invention provides differentiated cell derived from a cloned, self-renewing pluripotent hepatic stem cell, or progeny thereof.

In a preferred embodiment, the differentiated cell of the present invention is selected from the group consisting of a hepatocyte, a cholangiocyte, a pancreatic ductal cell, an acinar cell, and an intestinal epithelial cell.

The methods for differentiation are well known in the art and are reviewed in the following references: Chen, J. R., M. S. Tsao, and W. P. Duguid. 1995. Hepatocytic differentiation of cultured rat pancreatic ductal epithelial cells after in vivo implantation. *Am. J. Pathol.* 147: 707–717. ; Crosby, H. A., D. A. Kelly, and A. J. Strain. 2001. Human hepatic stem-like cells isolated using c-kit or CD34 can differentiate into biliary epithelium. *Gastroenterology* 120: 534–544; Dabeva, M. D., P. M. Petkov, J. Sandhu, R. Oren, E. Laconi, E. Hurston, and D. A. Shafritz. 2000. Proliferation and differentiation of fetal liver epithelial progenitor cells after transplantation into adult rat liver. *Am. J. Pathol.* 156: 2017–2031; Rao, M. S., R. S. Dwivedi, A. V. Yeldandi, V. Subbarao, X. D. Tan, M. I. Usman, S. Thangada, M. R. Nemali, S. Kumar and D. G. Scarpelli. 1989. Role of periductal and ductular epithelial cells of the adult rat pancreas in pancreatic hepatocyte lineage. A change in the differentiation commitment. *Am. J. Pathol.* 134: 1069–1086; and Zulewski., H., E. J. Abraham, M. J. Gerlach, P. B. Daniel, W. Mortitz, B. Muller, M.Vallejo, M. K. Thomas, and J. F. Habener. 2001. Multipotential nestin-positive stem cells isolated from adult pancreatic Islets differentiate ex vivo into pancreatic endocrine, exocrine, and hepatic phenotypes. *Diabetes* 50: 521–533.

In an alternative aspect of the invention, the present invention provides a tissue regenerated from a cloned, self-renewing pluripotent hepatic stem cell, or progeny thereof. Preferably, the tissue is a liver tissue. In other aspect of the invention, the present invention provides an organ regenerated from a cloned, self-renewing pluripotent hepatic stem cell, or progeny thereof. In a preferable embodiment, the organ Is a liver.

Regeneration methods are well known in the art, and those skilled in the art are able to select an appropriate method for a desired purpose without undue experimentation. In an exemplified embodiment, the present stem cells are injected into a site of a recipient host, and let the stem cell stand for a certain period of time in order to regenerate into a tissue or organ. Such methods are well reviewed in the following references: Fausto, N., and E. M. Webber. 1994. Liver regeneration : *The Liver*. I. M. Arias, J. L. Boyer, N. Fausto, W. B. Jakoby, D. A. Schachter, and D. A. Shafritz, editors : Raven Press. N.Y., ed. 3. 1059–1084; Fujio, K., R. P. Evarts, Z. Hu. E. R. Marsden, and S. S. Thorgeirsson. 1994. Expression of stem cell factor and its receptor, c-kit, during liver regeneration from putative stem cells in adult rat. *Lab. Invest.* 70: 511–516; Michalopoulos, G. K., and M. C. DeFrances. 1997. Liver regeneration. *Science* 276: 60–66; Omori, N., M. Omori, R. P. Evarts, T. Teramoto, M. J. Miller, T. N. Hoang, and S. S. Thorgeirsson. 1997. Partial cloning of rat CD34 cDNA and expression during stem cell-dependent liver regeneration in the adult rat. *Hepatology* 26, 720–727; Overturf, K., M. Al-Dhalimy, C. N. Ou, M. Finegold, and M. Grompe. 1997. Serial transplantation reveals the stem-cell-like regenerative potential of adult mouse hepatocytes. *Am. T. Pathol.* 151: 1273–1280.; and Thorgeirsson, S. S. 1996. Hepatic stem cells in liver regeneration. *FASEB J.* 10: 1249–1256.

In a further aspect, the present invention provides a method of transplanting cells into a recipient host, comprising obtaining a cloned, self-renewing pluripotent hepatic stem cell, or progeny thereof: and transplanting said stem cell into the host.

In yet a further aspect, the present invention provides a method of transplanting a tissue into a recipient host, comprising: obtaining a cloned, self-renewing pluripotent hepatic stem cell, or progeny thereof; regenerating a tissue from the stem cell; and transplanting said tissue into the host. In a preferred embodiment, said tissue is a liver tissue.

In a still further aspect, the present invention provides a method of transplanting an organ into a recipient host, comprising: obtaining a cloned, self-renewing pluripotent hepatic stem cell, or progeny thereof; regenerating an organ from the stem cell; and transplanting said organ into the host. In a preferred embodiment, said organ is a liver or bile duct.

Transplantation methods are well known in the art, and can be referred to: Dabeva, M. D., P. M. Petkov, J. Sandhu, R. Oren, E. Laconi, E. Hurston, and D. A. Shafritz. 2000. Proliferation and differentiation of fetal liver epithelial progenitor cells after transplantation into adult rat liver. *Am. J. Pathol.* 156: 2017–2031; Grisham, J. W., W. B. Coleman, and G. J. Smith. 1993. Isolation, culture, and transplantation of rat hepatocytic precursor (stem-like) cells. *Proc. Soc. Exp. Biol. Med.* 204: 270–279 Overturf, K., M. Al-Dhalimy, C. N. Ou, M. Finegold, and M. Grompe. 1997. Serial transplantation reveals the stem-cell-like regenerative potential of adult mouse hepatocytes. *Am. J. Pathol.* 151: 1273–1280.

(Clonal fractionation of H-CFU-C)

Self-Renewal of H-CFU-C In Vitro and In Vivo

As exemplified below in Examples, in vitro clonal subculture analysis showed that a single sorted H-CFU-C generated many Individual daughter cells, giving rise both to binucleate albumin-positive hepatocytes and to cytokeratin 19-positive, cholangiocytes that formed duct-like structures. Study on the secondary colonies by transmission electron microscopy also showed that they were capable of differentiating into hepatocytes, forming bile canaliculi-like structures with luminal spaces occupied by microvilli, and into cholangiocytes, forming well-organized bile duct-like structures with luminal membranes covered with short microvilli. Moreover, when we conducted re-cloning experiments using cells derived in turn from a single daughter cell, we obtained similar results. These data clearly show that H-CFU-C underwent self-renewing divisions while retaining multilineage differentiation potential in vitro. Most colonies derived from progeny of a H-CFU-C expressed neither albumin nor cytokeratin 19 for up to 14 days in culture. By day 21 of culture, however, they gave rise to cells in two lineages, each expressing one of these markers. This pattern of differentiation parallels that of primarily cultured H-CFU-C; even when propagated for longer periods, colony-repopulating cells normally began to proliferate while expressing neither of these markers and slowly generated lineage-committed progeny in vitro.

Hematopoietic stem cells can reconstitute all types of blood cells in sublethally irradiated mice without being cultured in vitro. Transplantation of a single stem cell clearly demonstrated that such cells could generate a subpopulation of their own cell type by self-renewing divisions in vivo (Osawa et al., 1996). Although the H-CFU-C described here have the potential to self-renew in vitro, it has not been directly confirmed that this property reflects the potential for self-renewing cell division in vivo. It has not yet been technically possible to transplant a single H-CFU-C and thereby directly to analyze the self-renewing potential of such a cell in vivo. However, by combining in vivo BrdU incorporation with in vitro functional assays of c-Met$^+$ CD49f$^{+/low}$ c-Kit$^-$ CD45$^-$ TER119$^{31}$ cells, we found that at least half the population of such cells is capable of self-renewing cell division in the ED 12.75 to ED 13.5 developing liver. This result also demonstrates that self-renewing H-CFU-C is very rare, even in early liver development. The numbers of H-CFU-C present In the fetal liver increase at most 7-fold through ED 11.5 to ED 13.5, then remain steady until ED 15.5. We concluded that H-CFU-C are mostly self-renewing early in liver organogenesis, and that they then divide more slowly, shifting to the production of committed progenitors that, In their turn, proliferate and differentiate relatively rapidly in subsequent liver development.

The present invention has shown that H-CFU-C Differ from Previously Described Hepatic Stem-like Cell Lines.

Like other tissue-specific stem cells, H-CFU-C can maintain themselves in culture and continuously give rise to hepatocytes and cholangiocytes. Although several bi-potent hepatic stem-like cell lines have been isolated from normal and malignant hepatic tissues (Pack et al., 1993 Grisham et al., 1993), evidence has been lacking as to whether they normally resided in liver or accidentally emerged following the process of immortalization in culture. In the present work, we repeatedly isolated and clonally propagated large numbers of H-CFU-C from fetal mouse liver. In the c-Met$^+$ CD49f$^{+/low}$ c-Kit$^-$ CD45$^-$ TER119$^-$ cell subpopulation, nearly 60% of H-CFU-C were subcultured and propagated in vitro, with few morphological and functional differences among them. We also found the same cell subpopulation to be enriched in H-CFU-C in various mouse strains, and propagated H-CFU-C routinely. Following cell transplantation, even into mice with immunodeficiency, we have never found abnormal development and tumor formation by donor-derived cells. These results strongly suggest that H-CFU-C do not appear transiently, are not strain-specific, and are not the product of transformation; instead, they normally exist in the cell subpopulation within developing mouse livers that is phenotypically distinguished as c-Met$^+$ CD49f$^{+/low}$ c-Kit$^-$ CD45$^-$ TER119$^-$;

H-CPU-C may Represent a Primitive Pluripotent Stem Cell Persisting in the Developing Mouse Liver.

Sequential histologic analyses suggested that the hepatoblasts in ED 13.5 developing mouse liver have already expressed albumin and □-fetoprotein, and that these cells still were capable of differentiation into cholangiocytes (Shiojiri et al., 1991). Our data show that hepatic stem cells defined as H-CFU-C exist in the developing liver without expression of both hepatocyte and cholangiocyte lineage markers. It also demonstrated that such cells were much fewer than previously hypothesized and their numbers appear to decrease as gestation advances. These findings may suggest that H-CFU-C differ from hepatoblasts that express several lineage markers and largely occupy the developing liver.

We transplanted cells derived from clone-sorted H-CFU-C. Although we did not conduct single H-CFU-C transplantation, our results show that cells derived from a single H-CFU-C reconstituted hepatocytic, bile-ductal, pancreatic, and intestinal structures following in viva differentiation into cells of each lineage. Especially in pancreas and intestine, they differentiated into cells in pancreatic ducts and cells residing near the base of crypt in intestinal epithelium, generally thought as pancreatic or intestinal epithelial stem cells. In this cell transplantation study, few EGFP-positive islet-forming cells were seen in vivo. However, expression of insulin, glucagon, and somatostatin, marker for pancreatic α, β, and γ cells, was detectable by RT-PCR in culture of those clones. The adult pancreatic environment may not support differentiation of islet-forming cells from H-CFU-C or it may be that an adequate tissue injury is required for islet reconstitution. Alternatively, islet-specific transgene silencing may have occurred during the differentiation process. We also found the expression of fabp-2 and secretin, and pepsinogen F, expressed in intestine and stomach. These results suggest that a few self-renewing pluripotent stem cells remained in the later gestational stage, even after the specification of liver, pancreas, stomach and intestine from endoderm layer. While there is no evidence that there is a hierarchy of lineage progression between hepatoblasts and more primitive cells, H-CFU-C could be considered as the equivalent to a pluripotent endodermal stem cells maintained by their own self-renewal capability in the developing liver.

The present Invention Demonstrated the Use of Pluripotent Stem Cells as their Importance to Stem Cell Biology and Therapeutic Strategies.

The cell-based study of stem cells in mammalian solid organs is generally considered difficult, because the constituent cells of these organs adhere tightly to one another and because cells of many lineages are present. Progress in organ-specific stem cell biology has been correspondingly slow. Cell populations enriched in prospectively identified liver stem cells can provide fundamental understanding of the characteristics of such cells, such as what signals determine their lineage commitment, what genes are driven when differentiation or self-renewal occurs, and whether they divide symmetrically or asymmetrically in vivo or in vitro. They also provide a powerful tool and information for developing therapeutic strategies, such as gene therapy, cell therapy, and the treatment of organ failure by using manipulated somatic stem cells or embryonic stem cells. In this invention, to trace donor-derived cells following cell transplantation, we infected hepatic stem cells with a retrovirus and marked them for EGFP expression In vitro; single virus infection reproducibly achieved nearly complete tagging. This highly efficient gene transfer method may supply a tool for examination of critical genes in differentiation or self-renewal. In addition, gene-modified stem cells are theoretically useful for clinical gene therapy. Identification of self-renewing pluripotent stem cells that can be propagated in vitro could allow us to describe endodermal cell lineages precisely, and to reveal the molecular mechanisms involved in self-renewal and differentiation.

A pluripotent stem cell may be defined as follows: (1) gives rise to progeny In all defined hepatic lineages; and (2) limiting numbers of cells are capable of fully reconstituting a seriously immunocompromised human host in all hepatic cell types and their progenitors, including the pluripotent hepatic stem cell by cell renewal. In the subject compositions, fewer than a total of about $10^7$ cells, usually fewer than $10^6$ cells, may be used to reconstitute an immunocompromised human host. The number of cells is required to insure that appropriate seeding at an appropriate site occurs, where the stem cell may self-renew. The number of cells required which become seeded at a proper site for self-renewal may be fewer than 50 cells, and as few as about a total of 20 cells or fewer, or even a single cell, are able to fulfill the conditions indicated above. Thus, based on the standards set for the earliest progenitor pluripotent stem cell, the subject compositions are capable of fulfilling these requirements.

Once stem cells have been isolated or cloned, they may be propagated by growing in conditioned medium from stromal cells, such an stromal cells that can be obtained from the liver or fetal liver, and are shown to provide for the secretion of growth factors associated with stem cell maintenance, coculturing with such stromal cells, or in medium comprising maintenance factors supporting the proliferation of stem cells, where the stromal cells may be allogeneic or xenogeneic. Before using in the coculture, the mixed stromal cell preparations may be freed of hepatic cells employing appropriate monoclonal antibodies for removal of the undesired cells, e. g, with antibody-toxin conjugates, antibody and complement, etc. Alternatively, cloned stromal cell lines may be used where the stromal lines may be allogeneic or xenogeneic.

The subject cell compositions may find use in a variety of ways. Since the cells are naive, they can be used to reconstitute fully an irradiated host and/or a host subject to chemotherapy; or as a source of cells for specific lineages, by providing for their maturation, proliferation and differentiation into one or more selected lineages by employing a variety of factors, including various kinds of cytokines such as HGF, interleukins, e. g., IL-1, -2, -3, -4, -5, -6, -7, -8, etc., Leukemia Inhibitory Factory (LIF), Stem cell Factor (SCF), or the like, or stromal cells associated with the stem cells becoming committed to a particular lineage, or with their proliferation, maturation and differentiation.

The stem cells may also be used in the isolation and evaluation of factors associated with the differentiation and maturation of hepatic cells. Thus, the stem cells may be used in assays to determine the activity of media, such as conditioned media, evaluate fluids for cell growth activity, Involvement with dedication of particular lineages, or the like.

The stem cells of the present invention can be used for the treatment of hepatic diseases, disorders or conditions including but not limited to: alcoholic liver disease, hepatitis (A, B, C, D, etc.), focal liver lesions, primary hepatocellular carcinoma, large cystic lesions of the liver, focal nodular hyperplasia granulomatous liver disease, hepatic granulomas, hemochromatosis such as hereditary hemochromatosis, iron overload syndromes, acute fatty liver, hyperemesis gravidarum, intercurrent liver disease during pregnancy, intrahepatic cholestasis, liver failure, fulminant hepatic failure, jaundice or asymptomatic hyperbilirubinemia, injury to hepatocytes, Crigler-Najjar syndrome, Wilson's disease, alpha-1-antitrypsin deficiency, Gilbert's syndrome, hyperbilirubinemia, nonalcoholic steatohepatitis, porphyrias, noncirrhotic portal hypertension, noncirrhotic portal hypertension, portal fibrosis, schistosomiasis, primary biliary cirrhosis, Budd-Chiari syndrom, hepatic veno-occlusive disease following bone marrow transplantation, etc.

The stem cells may be used for the treatment of genetic diseases, Genetic diseases associated with hepatic cells may be treated by genetic modification of autologous or allogeneic stem cells to correct the genetic defect. Among the hepatic diseases listed above, any genetic disase may be corrected by introduction of a wild-type gene into the stem cells, either by homologous or random recombination. With allogeneic stem cells, normal cells lacking the genetic defect can be used as a therapy. Other indications of gene therapy are introduction of drug resistance genes to enable normal stem cells to have an advantage and be subject to selective pressure, e. g. the multiple drug resistance gene (MDR). Diseases other than those associated with hepatic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products.

For hepatic pathogens, such as HBV, HCV, etc. the stem cells of the present invention could be genetically modified to introduce an antisense sequence or ribozyme which would prevent the proliferation of the pathogen in the stem cell or cells differentiated from the stem cells.

Methods for recombination in cells may be found in Molecular Cloning, A Laboratory Manual (1989) Sambrook, Fritsch and Maniatis, Cold Spring Harbor, N.Y.

The cells may be frozen at liquid nitrogen temperatures and stored for long periods of time, being thawed and capable of being reused. The cells will usually be stored in 10% DMSO, 70% autologous plasma (irradiated with 2500 rad), 20% Tcl99 (Tissue culture medium). Cells are frozen in a programmable cell freezer to −180° C. in liquid nitrogen. Once thawed, the cells may be expanded by use of growth factors or stromal cells associated with stem cell proliferation and differentiation The hepatic stem cells, either autologous or allogeneic, may be used for treatment of various diseases where toxic is therapies may be involved. For example, in the treatment of neoplasia, liver may be removed from the patient (autologous) or from a "matched" donor ("allogeneic") and the stem cells isolated and optimally frozen. The patient's liver may be partially or wholly ablated using irradiation and/or chemotherapy. Once the treatment is completed, the stem cells may be thawed, if appropriate, administered to the patient by any convenient means, e g., intravascularly, in a physiologically acceptable medium. The patient may then be monitored for signs of engraftment.

The stem cells may be grown in culture, whereby the stem cells may be expanded. In this way, one can repetitively administer stem cells during a course of a toxic therapy.

The following examples are offered by way of illustration and not by way of limitation.

EXAMPLES

Example 1

Flow Cytometric Fractionation of Fetal Mouse Liver Cells

In this example, we fractionated H-CFU-H according to the method that we have previously reported (Suzuki et al., 2000), and thereafter we attempted to sort for cells expressing c-Met, the hepatocyte growth factor (HGF) receptor for further fractionation.

(Fractionation of "H-CFU-C" by Flow Cytometry) Cell preparation

Single cell suspensions of liver cells were prepared from Balb/cA ED13.5 fetal mice (CLEA, Tokyo, Japan). For sequential analysis, we used embryonic day (ED) 11.5, 13.5, 15.5, and neonatal (1 day after birth) mice. For sorting, we used mechanical pipetting in staining medium (PBS containing 3% FBS). Cell viability after each treatment was exceeded 90% as assessed by trypan blue dye exclusion.

Cell Staining and FACS Analysis

Dissociated liver cells were incubated at 4° C. for 30 minutes with biotinylated anti-CD45 and TER119 mAb (PharMingen, San Jose, Calif.), and anti-c-Met mAb (Upstate Biotechnology, Lake Placid, N.Y.).

After 3 washings with staining medium, cells were incubated with phycoerythrin (PE)-conjugated anti-CD49f mAb (PharMingen), fluorescein isothiocyanate (FITC)-conjugated anti-CD29 mAb (PharMingen), allophycocyanin (APC)-conjugated anti-c-Kit mAb (PharMingen), streptavidin-labeled Texas Red (Gibco BRL, Gaithersburg, Md.), at 4° C. for 30 minutes. For cells from EGFP transgenic mice, we used mAbs for CD45 (Cy-chrome) (PharMingen), c-Kit (APC), TER119 (APC) (PharMingen), CD49f (PE), c-Met, and mouse $IgG_{2a}$ (biotinylated) (PharMingen), and streptavidin-labeled Texas Red.

Finally, cells were washed 3 times and resuspended in staining medium containing propidium iodide (PI) (5 µg/ml) Labeled cells were analyzed and separated with FACSvantage (Becton Dickinson, San Jose, Calif.). Gating was implemented based on negative control staining profiles.

Cells in ED 13.5 fetal mouse liver cells which co-express CD49f and CD29 (α6 and β1 integrin subunits) but do not express c-Kit (stem cell factor receptor), CD45 (leukocyte common antigen)., or TER119 (a molecule resembling glycophorin and exclusively expressed on immature erythroid cells) are the best candidate hepatic stem/progenitor cells as we reported previously (Suzuki et al., 2000).

Sorting for c-Kit$^-$ CD49f$^+$ CD29$^+$ CD 45$^-$ TER119$^-$ cells has achieved 34.9-fold enrichment of H-CFU-C compared to total fetal liver cells.

In order further to enrich the yield of H-CFU-C and thereby to permit clonal analysis of this cell class, as well as to examine such cells' capacity for self-renewal and differentiation, we attempted in the present example to sort for cells expressing c-Met, the HGF receptor. During mammalian organogenesis, HGF and c-Met interaction mediates a signal exchange between mesenchymal and epithelial cells in the developing liver (Hu Z. et al., 1993; Johnson M. et al., 1993; Schmidt C. et al., 1995). In embryonic mice lacking HGF, placental defects and liver abnormalities were observed (Uehara Y. et al., 1995). In addition, HGF was a critical requirement for the proliferation of H-CFU-C; its absence was not compensated for by EGF or other cytokines (Suzuki et al., 2000; and unpublished data). These findings led us to speculate that cells expressing c-Met have an essential role in the developing mouse liver.

Cell Sorting by FACS for c-Met and CD49f Expression c-Kit$^{31}$ CD45$^-$ TER119$^-$ cells among ED 11.5, ED 13.5, and ED 15.5 fetal mouse liver cells were fractionated by c-Met and CD49f expression. Sorting gates were then set for c-Met$^-$ CD49f$^-$, c-Met$^-$ CD49f$^{+/low}$, c-Met$^-$ CD49f$^{+/high}$, c-Met$^+$ CD49f$^{31}$ c-Met$^+$ CD49f$^{+/low}$, and c-Met$^+$ CD49f$^{+/high}$ subpopulations. The percentage of fractionated cells is shown at upper right. Representative data from 6 independent experiments are shown in FIG. 1A.

Figure 1B:
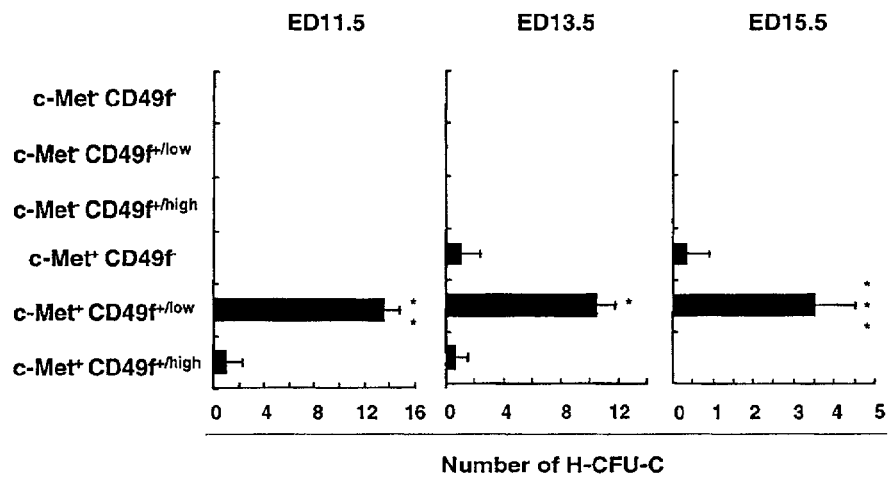
Figure 3A:
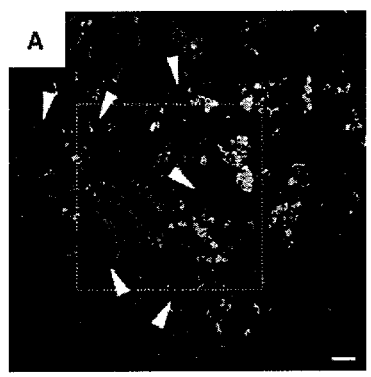
FIG. 3. Multipotency of re-clone-sorted progeny derived from a single H-CFU-C. Subcultured cells derived from a H-CFU-C were clone-sorted again and subjected to single cell culture. (A-C) Re-sorted cells gave rise to albumin-positive hepatocytes (shown in green) cytokeratin 19-positive cholangiocytes (shown in red) after 21 days of culture. As upon primary culture, they gave rise to albumin and cytokeratin19double-positive cells (shown in yellow) and to double-negative cells. Duct-like structures formed by cells expressing cytokeratin19(A, arrowheads), and binucleate cells (B. arrowheads), interpreted as mature hepatocytes were regularly observed. (D) Twenty-three individual colonies (12 colonies cultured on laminin-coated, 11 on type IV collagen-coated 96-well plates) were examined by RT-PCR at day 21. Frequencies of positive colonies are indicated. (E) Ultrastructural study of the progeny of re-clone-sorted cells found many ovoid mitochondria and glycogen rosettes in their cytoplasm. Adjacent cells also formed well-defined narrow lumina with numerous microvilli and intracellular tight junctional complexes (arrows). These structures resembled hepatic bile canaliculi. (F-G) Bile duct-like structures formed by neatly aligned cells were morphologically characterized by frequently notched nuclei at the basal aspects; a relatively large nucleus: cytoplasm ratio; numerous short microvilli projecting into luminal regions (G, arrowheads); and close attachment, with juxtaluminal junctional complexes between adjacent cells (G, arrows). Scale bar: (A-C) 100 μm, (E) 2 μm, and (F-G) 10 μM FIG. 4. H-CFU-C incorporated BrdU in vivo while retaining the capacity for multilineage differentiation. (A) FACS analysis of cells that had incorporated BrdU after pulse-labeling from ED 12.75 to ED 13.5. Most sorted unfractionated and c-Met⁺ CD49f$^{+/low}$ c-Kit⁻ CD45⁻ TER119⁻ cells isolated from BrdU-treated mice were BrdU-positive. Representative data are shown. (B-C) Ten to twelve hours after c-Met⁺ CD49f$^{+/low}$ c-Kit⁻ CD45⁻ TER119⁻ cells were plated, most attaching (but not dividing) cells were BrdU-positive. (D-E) In sections of BrdU-treated ED 13.5 fetal mouse liver, almost all liver cells were BrdU-positive. Scalebar: (B-C) 25 μm, (D-E) 100 μm.
Figure 3B:
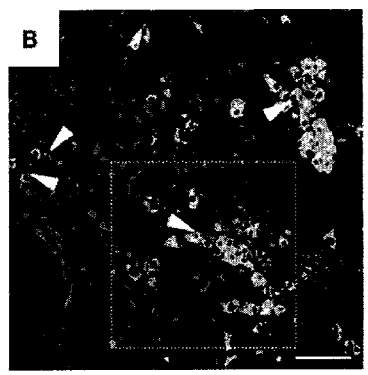
Figure 3C:
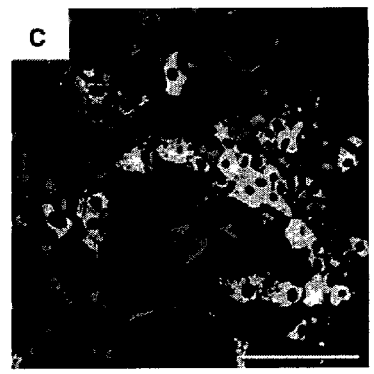
Figure 3D:
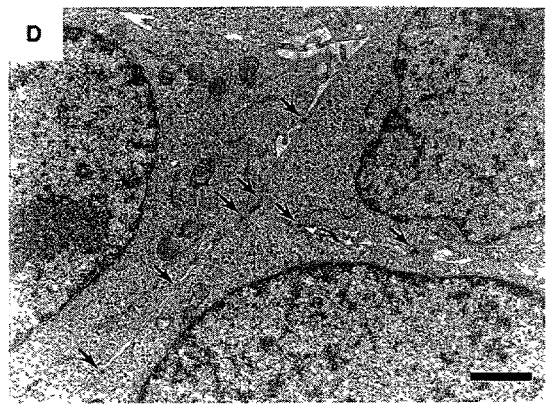
Figure 3F:
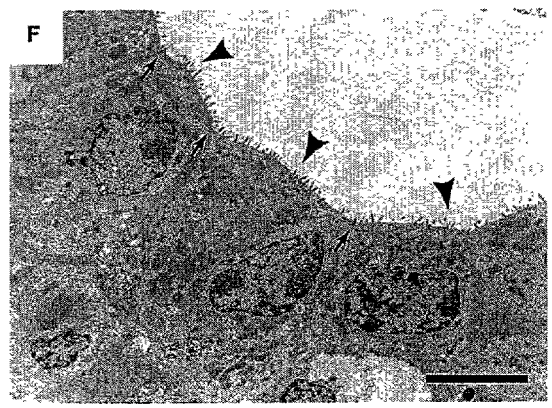
Figure 3E:
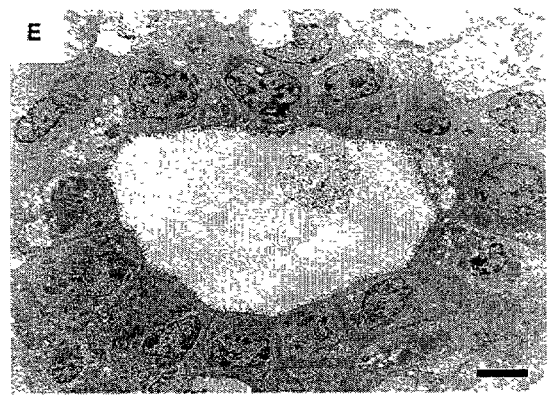

We fractionated c-Kit$^-$ CD45$^-$ TER119$^-$ cells (5.05 ±1.72%) in ED 13.5 fetal mouse livers into 6 subpopulations by using antibodies against c-Met and CD49f in combination: (i) c-Met$^+$ CD49f$^{+/high}$ cells (0.05±0.01%); (ii) c-Met$^+$ CD49f$^{+/low}$ cells (0.30±0.05%); (iii) c-Met$^+$ CD49f$^-$ cells (0.02±0.02); (iv) c-Met$^-$ CD49f $^{+/high}$ cells (0.14±0.03%) (V) c-Met$^-$ CD49f$^{+/low}$ cells (1.90±0.33%); and (vi) c-Met$^-$ CD49f$^-$ cells (1.19±0.45%) (FIG. 1 A). Under clonal density culture conditions of 30 cells/cm$^2$, H-CFU-Cs were mostly found in the c-Met$^+$ CD49f$^{+/low}$ c-Kit$^-$ CD45$^-$ TER119$^-$ cell subpopulation (FIG. 1 B). Sorting for c-Met$^+$ CD49f$^{+/low}$ c-Kit$^-$ CD45$^-$ TER119$^-$ cells achieved 560-fold enrichment in H-CFU-C by comparison with total fetal liver cells. These results were not limited to ED 13.5 fetal mice. In both ED 11.5 and ED 15.5 mouse liver, H-CFU-C were also found in the same cell subpopulation (ED 11.5: 1.54±0.02%, ED15.5: 0.21±0.02%) (FIG. 1 A-B).

As shown above, the present example demonstrated that sorting for c-Met$^-$ CD49f$^{+/low}$ c-Kit$^-$ CD45$^-$ TER119$^-$ cells permits us to obtain clonal identification and characterization of self-renewing pluripotent stem cells in the developing liver.

Example 2

Characterization of c-Met$^+$ CD49f$^{+/low}$ c-Kit$^-$ CD45$^-$ TER119$^-$ cells In the present example, we characterized of c-Met$^+$ CD49f$^{+/low}$ c-Kit$^-$ CD45$^-$ TER119$^-$ cells.

High enrichment in H-CFU-C achieved in Example 1 permitted efficient culture of clone-sorted c-Met$^+$ CD49f$^{+/low}$ c-Kit$^-$ CD45$^-$ TER119$^-$ cells for analyses of self-renewal and differentiation potential.

For low density culture analysis, sorted cells were plated on laminin-coated 6-well plates (Becton Dickinson) at a density of 30 cells/cm$^2$ and cultured in our fresh standard medium (1:1 mixture of DMEM and F-12 (Sigma, Chemical Co., St. Louis, Mo.) with 10% fetal bovine serum (JRH BIOSCIENCES, Lenexa, Kans., γ-insulin (1 μg/ml) (Wako, Tokyo, Japan), dexamethasone (1×10$^{-7}$ M) (Sigma), nicotinamide (10 mM) (Sigma), L-glutamine (2 mM) (Gibco BRL, Gaithersburg, Md.), β-mercaptoethanol (50 μM) (Sigma), HEPES (5 mM) (Wako), and penicillin/streptomycin (Gibco BRL)). For single cell culture analysis, we used standard medium 50% supplemented with medium conditioned by 7-day culture of non-sorted (total) fetal liver cells. Both culture media included human recombinant hepatocyte growth factor (HGF) (50 ng/ml) (Sigma Chemical Co., St. Louis, Mo.) and epidermal growth factor (EGF) (20 ng/ml) (Sigma). Viability of sorted cells exceeded 90% as assessed by trypan blue exclusion. Residual erythrocytes, debris, doublets, and dead cells were excluded by forward scatter, side scatter, and PI gating. The number of colonies was determined after 5 days of culture, "hepatic colony-forming unit in culture (H-CFU-C)" is defined herein as a colony containing over 100 cells.

Cells identified on clone-sorting by flow cytometry were cultured in individual wells of laminin-coated 96-well plates as explained above. To ascertain that single cells have been deposited, we always examine each well to confirm the presence of a single cell under the microscope after clone-sorting. Once a cell sorter is adjusted for optimal setting prior to the experiment, we seldom find wells with more than 2 cells after clone-sorting. In one series of experiments, we found one well that had 2 cells out of 4000 wells. We have never found 3 cells in a well. When we found these wells, we excluded them from samples for analysis.

As in clonal density culture, relatively large colonies (>100 cells) derived from H-CFU-C in a truly clonal manner were observed (FIGS. 2A–C). Not only H-CFU-C colonies were present; colonies containing from 50 to 100 cells ("medium colonies [MC]") and colonies containing <50 cells ("small colonies [SC]") also were seen. These different sizes of colonies, H-CFU-C colonies, MC, and SC, were formed by 5.88±3.57%, 6.56±3.19%, and 26.7±6.41% of sorted cells, respectively (average of 75 plates [7200 wells], 15 independent experiments).

To characterize the colonies, we stained colony-constituent cells at days 5 and 21 with antibodies against albumin or cytokeratin 19 as described previously (Suzuki et al., 2000). Briefly, cultured cells in each colony were washed 3 times with phosphate-buffered saline (PBS), fixed by methanol at −20° C. for 10 minutes, and washed in PBS including 0.05% polyoxyethylene (20) sorbitan monolaurate (Tween 20) (Wako). Nonspecific binding was blocked with 10% non-immune serum of a species from which the secondary antibody had been obtained. Fixed cells were incubated with primary antibody rabbit anti-albumin (Biogenesis, Poole, UK) and mouse anti-cytokeratin 19 (Amersham, Little Chalfont, UK), in a moist chamber for 16 h at 4° C. After washing in PBS-Tween 20 and blocking, cells were incubated with Alexa 488-conjugated goat anti-rabbit IgG (Molecular Probes, Eugene, Oreg.) and Cy3-conjugated goat anti-mouse IgG (Jackson ImmunoResearch Laboratories, Inc., West Grove, Pa.) for 3 h at 4° C. After final washing, cells were viewed using a Zeiss LSM510 laser scanning microscope, At day 5of culture, immunocytochemistry revealed that most SC was composed of cells expressing either albumin or cytokeratin 19(FIGS. 2 D–E). In contrast cells expressing neither formed most H-CFU-C colonies (FIG. 2 F), except for a few multicolor-stained colonies (FIG. 2 G). Cells In H-CFU-C colonies continued to proliferate intensively for about 2 weeks, and then reached near-plateau. By day 21, most H-CFU-C eventually gave rise to cells: (i) marking only for albumin; (ii) marking only for cytokeratin 19; (iii) marking for both albumin and cytokeratin 19; (iv) marking for neither albumin nor cytokeratin 19 (FIGS. 2 H–J). However, a few H-CFU-C appeared already to have been committed at planting, as they generated only hepatocytes or cholangiocytes (FIGS. 2 K–L). Periodic acid~Schiff (PAS) staining (Lillie et al., 1976) showed that several cells derived from H-CFU-C were functionally mature hepatocytes, with abundant glycogen stores, at day 21 (FIGS. 2 M–N). The differentiation potential of cells forming MC appeared intermediate between that of H-CFU-C and that of cells forming SC. the cell profiles of colonies at days 5 and 21 are summarized in Table a These results of FACS® clone-sorting experiments suggest that most SC were formed by lineage-committed cells with limited potential for growth and differentiation, whereas H-CFU-C were capable of intensive growth and multilineage differentiation.

TABLE 1

Immunocytochemical analysis of varying differentiation potential among various-sized colonies derived from c-Met$^+$ CD49f$^{+/low}$ c-Kit$^-$ CD45$^-$ TER119$^-$ cells.

| Colony type | Cells in a colony | | | | |
|---|---|---|---|---|---|
| | Bipotent Alb- and Ck19-positive cells (%) | Unipotent Alb-positive cells (%) | Unipotent Ck19-positive cells (%) | No expression of Alb and Ck19 | Number of colonies examined |
| 5-d culture | | | | | |
| H-CFU-C | 7(22.6) | 1(3.2) | 5(16.1) | 18(58.1) | 31 |
| medium | 8(18.2) | 0(0) | 18(40.9) | 18(40.9) | 44 |
| small | 6(9.2) | 15(23.1) | 10(46.2) | 14(21.5) | 65 |

TABLE 1-continued

Immunocytochemical analysis of varying differentiation potential among various-sized colonies derived from c-Met+ CD49f+/low c-Kit− CD45− TER119− cells.

| | Cells in a colony | | | | |
|---|---|---|---|---|---|
| Colony type | Bipotent Alb- and Ck19- positive cells (%) | Unipotent Alb-positive cells (%) | Unipotent Ck19- positive cells (%) | No expression of Alb and Ck19 | Number of colonies examined |
| 21-d culture | | | | | |
| H-CFU-C | 20(76.9) | 1(3.85) | 1(3.85) | 4(15.4) | 26 |
| medium | 9(45.0) | 3(15.0) | 2(10.0) | 6(30.0) | 20 |
| small | 7(12.3) | 7(12.3) | 9(15.8) | 34(59.6) | 57 |

Clone-sorted c-Met+ CD49f+/low c-Kit− CD45− TER119− cells were cultured for 5 or 21 days, after which double-staining for albumin and cytokeratin 19 markers was conducted. At day 5, most H-CFU-C progeny had differentiated into neither hepatocytes nor cholangiocytes. However, following 21 days of culture, most H-CFU-C had given rise to cells of both lineages. In contrast, cells in SC differentiated rapidly into either hepatocytes or cholangiocytes at day 5, and rarely into both. Cells in half of the SC survived up to 21 days in culture, but they had al ready stopped growing and expressing albumin or cytokeratin 19. MC showed patterns of differentiation intermediate between those of H-CFU-c colonies and those of SC.

Example 3

Clonal Expansion and Self-Renewal Capability of H-CFU-C in Culture

We next used sub cloning experiments to test the self-renewal potential of H-CFU-C. Single c-Met+ CD49f+/low c-Kit− CD45− TER119− cells were clone-sorted and individually cultured. This yielded several large H-CFU-C colonies (see FIG. 2 C), which we then replated onto new culture dishes. Over 2 to 3 weeks, about half of subcultured clones gradually expanded, finally to become confluent. These clonally expanding subcultured cells then again underwent clone-sorting and single cell culture.

We then conducted detection of hepatocyte or cholangiocyte marker gene expression by RT-PCR as described previously in Suzuki at al., 2000. Briefly, a cloning ring (Iwaki Glass, Tokyo, Japan) was placed on the colony and total RNA was prepared by gentle pipetting cells with ISOGEN (Nippon Gene, Tokyo, Japan). Prior to reverse transcription, 0.8 μl of oligo-d(T)$_{1218}$ primers was added to the total RNA solution. The reaction mixture was heated at 75° C. for 5 min and then, for hybridization, incubated at 42° C. for 5 min. cDNA was synthesized from total RNA in 20 μl of reaction mixture containing 1×first strand buffer, 0.5 mM dNTP, 5 mM DTT, and 200 units of Super Script II (Gibco BRL). PCR was conducted in 25 μl of the reaction mixture (1×PCR buffer, Taq DNA polymerase) (Takara Shuzo Co., Tokyo, Japan), PCR cycles were as follows: initial denaturation at 95° C. for 4 min followed by 45 cycles of 94° C. for 1 min., 56° C. for 1 min, 72° C. for 1 min and final extension at 72° C. for 10 min. PCR products were separated in 1.7% agarose gel.

Hepatocyte-differentiation markers included albumin, α-fetoprotein, α-1-antitrypsin, glucose-6-phosphatase, and dipeptidylpeptidase IV. Cholangiocyte-differentiation markers included cytokeratin 19, thymosin β4 (5'-TGT CCA GCG CAG GCA CTT G-3' (SEQ ID NO.: 1) and 5'-CAA AGA TGT CCT GCA GGA TG-3' (SEQ ID NO.: 2)), biliary glycoprotein, γ-glutamyltranspeptidase, and vinculin. Miscellaneous markers included cytokeratin 18, cytokeratin 8, hepatocyte nuclear factor 1 (HNF-1) (5'-AAG CTG GTC TCA GCC ACG G-3' (SEQ ID NO.: 3) and 5'-CTG AGG TGA AGA CCT GCT T-3' (SEQ ID No.: 4)), HNF-3α (5'-GTC GCA AGG ACC CCT CAG G-3' (SEQ ID No.: 5) and 5'-CTT GAA GTC CAG CTT GTG CTG-3' (SEQ ID NO.: 6)), HNF-3β (5'-CTT CTC CGT GTC AGG AGC AC-3' (SEQ ID NO.: 7) and 5'-CTG GGT AGT GCA TGA CCT G-3' (SEQ ID NO.: 8)), NNF-3γ (5'-TCT GCC ACC ACT ACA GCT GC-3' (SEQ ID NO.: 9) and 5'-CGC TGC TAG GAT GCA TTA AGC-3' (SEQ ID NO.: 10), HNF-4 (5'-CTT CCA AGA GCT GCA GAT TG-3' (SEQ ID NO.: 11) and 5'-CTT GTA GGA TTC AGA TCC CG-3' (SEQ ID NO.: 12)), transthyretin (TTR) (5'-TGG TAT TTG TGT CTG AAG CTG-3' (SEQ ID No.: 13) and 5'-TTA ATA AGA ATG CTT CAC GGC-3' (SEQ ID NO.: 14)), c-met, and hypoxanthine phosphoribosyltransferase (HPRT) as a positive control. Mature hepatocyte functional gene expression was assessed using tryptophan-2, 3-dioxygenase (5'-TGC GCA AGA ACT TCA GAG TGA-3' (SEQ ID NO.: 15) and 5'-AGC AAC AGC TCA TTG TAG TCT -3' (SEQ ID NO.: 16)), glutathione S-transferase (5'-AAG TGA TGG GAG TCT GAT GTT-3' (SEQ ID NO.: 17) and 5'-TTC TTT GCT GAC TCA ACA CAT-3' (SEQ ID NO.: 18)), and glutamine synthetase (5'-AGT TAC CTG AGT GGA ACT TTG-3' (SEQ ID NO.: 19) and 5'-TTC GCA CAC CCG ATG CAA GAT-3' (SEQ ID NO.: 20)). Oval cell related gene expression was assessed using c-kit (5'-CCC AAG ACG TAA CAG CTT CTG-3' (SEQ ID NO.: 21) and 5'-CAG TCT CGT ACA TGA CCA CAG-3', (SEQ ID NO.: 22)), CD34 (5'-TCC TGA TGA ACC GTC GCA GTT G-3' (SEQ ID No .: 23) and 5'-TGT CAG CCA CCA CAT GTT GTC-3' (SEQ ID NO.: 24)), and thy-1 (5'-AGA AGG TGA CCA GCC TGA CA-3' (SEQ ID NO.: 25)and 5'-AAT GAA GTC CAG GGC TTG GA-3' (SEQ ID NO.: 26)). For analysis of pancreatic, intestinal, or gastric marker gene expression, PCR was conducted using primers for β cell markers: preproinsulin I (5'-CTG TTG GTG CAC TTC CTA CC-3' (SEQ ID NO.: 27) and 5'-GCA GTA GTT CTC CAG CTG GT-3' (SEQ ID NO.: 28)), preproinsulin II (5'-TCA AGC AGC ACC TTT GTG GTT-3' (SEQ ID No.: 29) and 5'-GTT GCA GTA GTT CTC CAG CTG-3' (SEQ ID NO.: 30)), and islet amyloid polypeptide (IAPP) (5'-TGT CCT CCT CAT CCT CTC TGT-3' (SEQ ID NO.: 31) and 5'-TAT GTA TTC GAT CCC ACG TTG-3' (SEQ ID No. 32)); α cell markers: preproglucagon (5'-ATT TAC TTT GTG GCT GGA TTG-3' (SEQ ID NO.: 33) and 5'-TGT CAG TGA TCT TGG TTT GAA-3' (SEQ ID NO.: 34)); δ cell marker: preprosomatostatin (5'-CTC TGC ATC GTC CTG GCT TT-3' (SEQ ID No.: 35) and 5'-CAG GAT GTG AAT GTC TTC CAG-3' (SEQ ID No.: 36)); exocrine lineage cell markers: amylase-2 (5'-AGT ACC TGT GGA AGT TAC CT-3' (SEQ ID NO.: 37) and 5'-ACA CAA GGG CTC TGT CAG AA-3 ' (SEQ ID NO.: 38) ), and hormone sensitive (HS)-lipase (5'-TCT TCT TCG AGG GTG ATG AA-3' (SEQ ID No .: 39) and 5'-TAC CTT GCT GTC CTG TCC TT-3' (SEQ ID NO.: 40)): pancreatic transcriptional factor genes: pancreas duodenal homeobox 1 (pdx-1) (5'-TTA CAA GCT CGC TGG GAT CAC-3' (SEQ ID No.: 41) and 5'-AGG TCA CCG CAC AAT CTT GCT-3' (SEQ ID No.: 42) ), neuroD/BETA2, and paired box transcription factor 6 (pax-6) (Jensen, J., E. E. Pedersen, P. Galante, J. Hald, R. S. Heller, M. Ishibashi, R. Kageyama, F. Guillemot, P. Serup, and O. D. Madsen. 2000. Control of endodermal endocrine development by Hes-1. Nat. Genet. 24: 36–44); intestinal or gastric lineage cell markers: intestinal fatty acid binding protein (fabp-2) (5'-ATT CGA CGG CAC GTG GAA AGT-3' (SEQ ID No.: 43) and 5'-AAG AAT CGC TTG GCC TCA ACT-3' (SEQ ID NO.: 44) ), secretin (5 '-AAG ACA CTC AGA CGG AAT GT-3 ' (SEQ ID NO.: 45) and 5'-TGG TTG TTT CAG TCC ACT CT-3' (SEQ ID NO.: 46)). gastric inhibitory peptide (GIP), cholecystokinin (CCX), gastrin (Jensen et al., 2000), and pepsinogen F (5'-ACC TAG ACC TGG TCT ACA TTG-3' (SEQ ID NO.: 47) and 5'-AGT GAA GCT CTC CAT GGT AGT-3' (SEQ ID NO.: 48)).

The results of the RT-PCT are shown In Table II.

albumin nor cytokeratin 19. On observation of colonies at day 21, however, most colonies (68.0%; n=25) were formed of both cells expressing albumin and cells expressing cytokeratin 19. Furthermore, albumin-positive cells with two nuclei and cytokeratin 19-positive cells forming duct-like structures appeared on day 21 of culture after re-sorting (FIGS. 3 A–C). Expression of several genes found in functionally mature hepatocytes was detected in re-sorted cell colonies (FIG. 3 D). Of interest is that expression of c-kit, CD34, and thy-1 became detectable in some of these colonies (FIG. 3 D). These results may suggest that oval cells, mark for c-Kit, CD34, and Thy-1 (Fujio, K., R. P. Evarts, Z. HU, E. R. Marsden, and S. S. Thorgeirsson. 1994. Expression of stem cell factor and its receptor, a-kit, during liver

TABLE II

Expression of lineage marker genes in colonies formed after reclone sorting

| | Laminin-coated dish | | | | | | | | | | | | | Type IV collagen-coated dish | | | | | | | | | | | |
|---|---|---|---|---|---|---|---|---|---|---|---|---|---|---|---|---|---|---|---|---|---|---|---|---|---|
| Colony number | 1 | 2 | 3 | 4 | 5 | 6 | 7 | 8 | 9 | 10 | 11 | 12 | % | 1 | 2 | 3 | 4 | 5 | 6 | 7 | 8 | 9 | 10 | 11 | % |
| Hepatocyte markers | | | | | | | | | | | | | | | | | | | | | | | | | |
| albumin | + | + | + | + | + | + | + | + | + | + | + | + | 100.0 | + | + | + | + | + | + | + | + | + | + | + | 100.0 |
| α-fetoprotein | + | + | + | + | + | + | + | + | − | + | + | + | 91.7 | + | + | + | + | + | + | + | + | + | + | + | 100.0 |
| α-1-antitrypsin | − | + | − | − | − | − | − | − | − | + | − | − | 16.7 | − | − | − | + | − | − | − | − | + | − | + | 36.4 |
| glucose-6-phosphatase | + | + | + | + | + | + | + | + | + | + | + | + | 91.7 | + | + | + | + | + | + | + | + | − | + | + | 81.8 |
| dipeptidylpeptidase IV | + | + | + | + | + | + | + | + | + | + | + | + | 100.0 | + | + | + | + | + | + | + | + | + | + | + | 100.0 |
| Cholangiocyte marker | | | | | | | | | | | | | | | | | | | | | | | | | |
| cytokeratin 19 | + | + | + | + | + | + | + | + | + | + | + | + | 100.0 | + | + | + | + | + | + | + | + | + | + | + | 100.0 |
| thymosin β4 | + | + | + | + | + | + | + | + | + | + | + | + | 100.0 | + | + | + | + | + | + | + | + | + | + | + | 100.0 |
| billary glycoprotein | + | + | + | + | + | − | + | + | + | + | + | + | 91.7 | + | + | + | + | + | + | + | + | + | + | + | 100.0 |
| γ-glutamyltranspeptidase | + | + | + | + | − | + | + | − | + | + | + | + | 83.3 | + | + | + | + | − | + | + | − | + | + | + | 81.8 |
| vinculin | + | + | + | + | + | + | + | + | + | + | + | + | 100.0 | + | + | + | + | + | + | + | + | + | + | + | 100.0 |
| Miscellaneous | | | | | | | | | | | | | | | | | | | | | | | | | |
| cytokeratin 18 | + | + | + | + | + | + | + | + | + | + | + | + | 100.0 | + | + | + | + | + | + | + | + | + | + | + | 100.0 |
| cytokeratin 8 | + | + | + | + | + | + | + | + | + | + | + | + | 100.0 | + | + | + | + | + | + | + | + | + | + | + | 100.0 |
| HNF-1 | + | + | + | + | + | + | + | + | + | + | + | + | 100.0 | + | + | + | + | + | + | + | + | + | + | + | 100.0 |
| HNF-3α | + | + | + | + | + | + | + | + | + | + | + | + | 100.0 | + | + | + | + | + | + | + | + | + | + | + | 100.0 |
| HNF-3β | + | + | + | + | + | + | + | + | + | + | + | + | 100.0 | + | + | + | + | + | + | + | + | + | + | + | 100.0 |
| HNF-3γ | + | + | + | + | + | + | + | + | + | + | + | + | 100.0 | + | + | + | + | + | + | + | + | + | + | + | 100.0 |
| HNF-4 | + | + | + | + | + | + | + | + | + | + | + | + | 100.0 | + | + | + | + | + | + | + | + | + | + | + | 100.0 |
| TTR | + | + | + | + | + | + | + | + | + | + | + | + | 100.0 | + | + | + | + | + | + | + | + | + | + | + | 100.0 |
| c-met | + | + | + | + | + | + | + | + | + | + | + | + | 100.0 | + | + | + | + | + | + | + | + | + | + | + | 100.0 |
| HPRT | + | + | + | + | + | + | + | + | + | + | + | + | 100.0 | + | + | + | + | + | + | + | + | + | + | + | 100.0 |
| Hepatocyte functional genes | | | | | | | | | | | | | | | | | | | | | | | | | |
| tryptophan-2,3-dioxygenase | + | − | − | − | + | − | + | − | − | − | − | − | 25.0 | + | + | − | − | + | − | + | − | + | + | − | 54.5 |
| glutathione S-transferase | − | − | + | + | − | − | + | − | + | + | + | + | 58.3 | − | − | − | + | + | − | + | − | + | + | − | 54.5 |
| glutamine synthetase | − | + | + | − | − | + | − | + | + | − | + | − | 50.0 | + | + | − | + | − | + | + | + | − | + | + | 72.7 |
| Oval cell-related genes | | | | | | | | | | | | | | | | | | | | | | | | | |
| c-kit | − | + | − | − | + | − | − | + | − | + | − | + | 41.7 | − | + | − | − | + | − | + | − | + | + | + | 54.5 |
| CD34 | − | + | + | − | − | − | − | − | + | − | − | − | 25.0 | + | − | − | + | + | − | − | − | − | + | − | 36.4 |
| thy-1 | + | + | − | − | + | − | − | − | − | + | − | − | 33.3 | − | − | − | + | + | + | − | − | − | + | + | 45.5 |

Twenty-three (23) individual colonies (twelve colonies cultured on laminin-coated and eleven on type IV colagen-coated 96 well plates) were examined by RT-PCR at day 21. Frequencies of positive colonies are indicated.

Surprisingly, many re-sorted cells (~15%) formed large colonies, and at day 21 had characteristics of multipotent cells on immunocytochemical and RT-PCP analysis (FIGS. 3 A–D). Sequential immunocytochemical analysis of colonies formed by re-sorted cells showed that most colonies observed at day 3 (83.3%; n=12 colonies assessed), at day 5 (93.8%; n=16), at day 8 (77.8%; n=9), and at day 14 (72.7% ; n=11) contained cells expressing neithe neither regeneration from putative stem cells in adult rat. Lab. Invest. 70: 511–516; Omori, N., M. Omori, R. P. Evarts, T. Teramoto, M. J. Miller, T. N. Hoang, and S. S. Thorgeirsson. 1997. Partial cloning of rat CD34 cDNA and expression during stem cell-dependent liver regeneration in the adult rat. Hepatology 26, 720–727; Petersen, B. E., J. P. Goff, J. S. Greenberger, and G. K. Michalopoulos. 1998. Hepatic oval cells express the hematopoietic stem cell marker Thy-1 In the rat. Hepatology 27: 433–445; Matsusaka, S., T. Tsujimura, A. Toyosaka, K. Nakasho, A. Sugihara, E. Okamoto, K. Uematsu, and N. Terada. 1999. Role of c-kit receptor tyrosine kinase in development of oval cells in the rat 2-acetylaminofluorene/partial hepatectomy model. Hepatology 29: 670–676), and are considered candidate hepatic stem/progenitor cells in adult liver (Sell, S., and H. A. Duneford. 1989. Evidence for the stem cell origin of hepatocellular carcinoma and cholangiocarcinoma. Am. J. Pathol. 134: 1347–1363; Fausto, 1994; Thorgeirsson, 1996Crosby et al., 2001), are close descendants of H-CFU-C.

Transmission electron microscopy of the progeny of a re-clone-sorted cell conducted as described (Suzuki et al., 2000), showed cells to be present that were largely occupied by well-developed ovoid mitochondria and that were attached closely to adjacent cells by intracellular tight junctional complexes (FIG. 3 E). These cells' borders defined luminal spaces densely decorated with microvilli, structures strongly resembling bile canaliculi between mature hepatocytes. The cells' cytoplasm also contained abundant glycogen. These observations demonstrated that cells among the progeny of re-sorted cells retained several morphologic and functional characteristics of hepatocytes. In addition to hepatocyte-lineage cells, we found many well-defined duct-like structures constituted of four to fifteen neatly aligned cells. These cells were characterized by a relatively large nucleus:cytoplasm ratio, numerous short microvilli, junctional complexes between adjacent cells, and a nucleus (frequently notched) that lay at the pole opposite to the apparent luminal space (FIGS. 3 F–G) These observations indicated that re-sorted cells gave rise to cells capable of forming bile duct-like structures. The various morphologic and functional characteristics described above clearly demonstrate that the progeny of single re-sorted cells could reconstitute hepatocyte or cholangiocyte microstructures In vitro. The results of immunocytochemical, RT-PCR, and ultrastructural analysis thus established that H-CFU-C in the phenotypically defined c-Met$^+$ CD49f$^{+/low}$ c-Kit$^-$ CD45$^-$ TER119$^-$ cell subpopulation have self-renewal potential as well as the capability of multilineage differentiation in vitro.

Example 4

In Vivo Self-Renewal of H-CFU-C in The Developing Mouse Liver

Because the self-renewing cells described here were isolated after expansion in culture for a relatively long period, it was possible that their self-renewal characteristics did not reflect their behavior in vivo. To clarify whether such cells are generated in vivo by division of cells with similar properties, we examined the in vivo self-renewing capability of H-CFU-C without in vitro explantation. In order to assay whether H-CFU-C were self-renewing in vivo, pregnant mice were administered the thymidine analogue bromodeoxyuridine (BrdU) 17 hr before harvest of fetal mouse liver cells (ED 12.75 to 13.5).

BrdU experiment was conducted as follows: BrdU (50 µg/g body weight) (Sigma) dissolved in 200 µl PBS with 0.007M NaOH (Morrison et al., 1999) was injected intraperitoneally at harvest −17 hr. −15 hr. −13 hr, −3.25 hr, −2.5 hr. −1.75 hr, and −1 hr. Additionally, from the first injection onward, drinking water given the mice contained 2 mg/ml of BrdU. Following the flow cytometric cell separation, sorted cells were fixed in 70% ethanol. After washing with PBS including 0.05% polyoxyethylene (20) sorbitan monolaurate (Tween 20) (Wako, Tokyo, Japan), the cells were treated with hydrochloric acid (4N) and neutralized in 0.1M sodium tetraborate (pH 8.5) (Sasaki, K., T. Murakami, and M. Takahashi. 1987. A rapid and simple estimation of cell cycle parameters by continuous labeling with bromodeoxyuridine. Cytometry 8: 526–528; Sasaki, K., S. Adachi, T. Yamamoto, T. Murakami, K. Tanaka, and M. Takahashi. 1988. Effects of denaturation with HCl on the immunological staining of bromodeoxyuridine incorporated into DNA. Cytometry 9: 93–96). The cells were then washed and stained with FITC-conjugated anti-BrdU antibody (Becton Dickinson) at room temperature for 30 minutes. Finally, after the cells were resuspended and incubated at 37° C. for 30 minutes in PBS containing RNase A (15 µg/ml) (Wako) and PI (5 µg/ml), analysis of the labeled cells was conducted by FACS-Calibur (Becton Dickinson). Short-term cultured non-divided cells and fetal liver frozen sections were stained with anti-BrdU antibody (Becton Dickinson) as described (Raff, M. C., L. E. Lillien, W. D. Richardson. J, F. Burne, and M. D. Noble. 1988. Platelet-derived growth factor from astrocytes drives the clock that times oligodendrocyte development in culture. Nature 333 : 562–565), using Cy3-conjugated goat anti-mouse IgG as a second antibody for visualization.

Figure 4A:
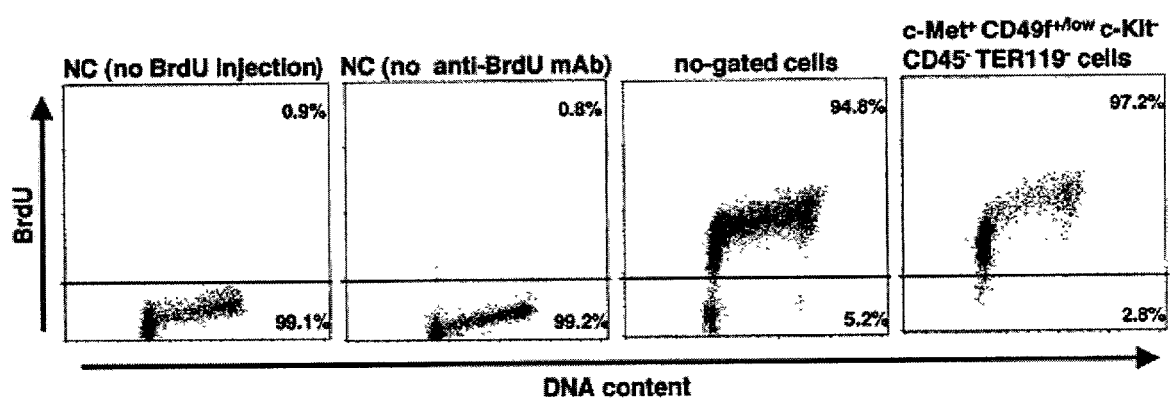
Figures 4B, 4C, 4D, 4E:
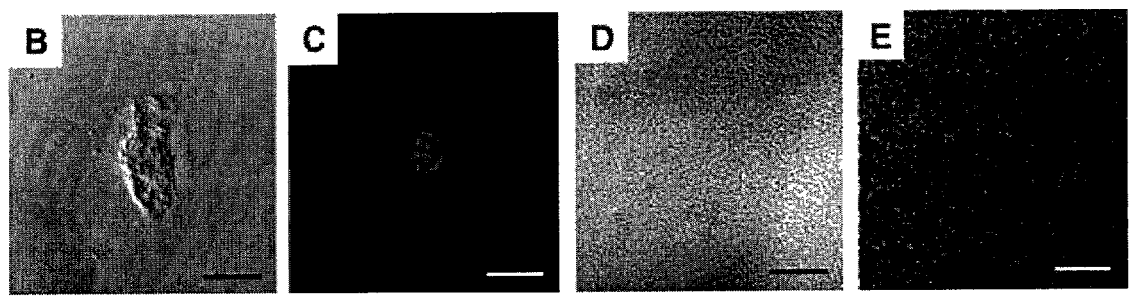

Results of the BrdU experiment are shown on FIG. 4. Unfractionated total fetal liver cells and c-Met$^+$ CD49f$^{+/low}$ c-Kit$^-$ CD45$^-$ TER119$^-$ cells, sorted by FACS, were directly fixed, stained, and analyzed for BrdU incorporation by FACS. Nearly 100% of both total fetal liver cells (93.0±2.75%; n=3) and c-Met$^+$ CD49f$^{+/low}$ c-Kit$^-$ CD45$^-$ TER119$^-$ cells (96.0±1.07%) incorporated BrdU over the 17-hr in vivo pulse (FIG. 4 A). In addition, sorted cells cultured for 10 to 12 hr and frozen sections from fetal liver following BrdU exposure were immunostained using an anti-BrdU antibody. As with results of FACS analysis, most cells that had successfully attached (91.3±1.61%) marked on immunostaining, as did cells in histologic sections of liver (FIGS. 4 B–E). To confirm that H-CFU-C isolated from fetal liver after BrdU exposure retained multilineage differentiation potential, we clone-sorted c-Met$^+$ CD49f$^{+/low}$ c-Kit$^-$ CD45$^-$ $^{TER}$119$^-$ cells and cultured them for 21 days. BrdU administration did not alter the number of H-CFU-C colonies, MC, and SC or their growth potential in vitro. Nor was there any significant change in FACS profiles between BrdU-treated and normal mice. We then double-stained H-CFU-C colonies to evaluate albumin and cytokeratin 19 expression and counted colonies with multilineage differentiation potential. In three independent experiments, we found 50, 36, and 45 colonies arising from 96 clonally cultured cells. Immunocytochemical examination of 23, 20, and 29 colonies respectively showed that 8, 7, and 10 colonies respectively continued to be multipotent in culture. The proportion of cells with multilineage differentiation potential was thus 8.68±1.59% (the average of 8.33%, 7.29%, and 10.4%) in sorted c-Met$^+$ CD49f$^{+/low}$ c-Kit$^-$ CD45$^-$ TER119$^-$ cells; it was 19.2±3.12% (the average of 16.0%, 19.4%, and 22.2%) in sorted, successfully attached cells. Since 96% of sorted c-Met$^+$ CD49f$^{+/low}$ c-Kit$^-$ CD45$^-$ TER119$^-$ cells and 91% of cultured cells incorporated BrdU in vivo, at least half of the c-Met$^+$ CD49f$^{+/low}$ c-Kit$^{31}$ CD45$^-$ TER119$^-$ cells retained multilineage differentiation potential following BrdU incorporation. These data clearly demonstrated that at least half of the c-Met$^+$ CD49f$^{+/low}$ c-Kit$^-$ CD45$^-$ TER119$^-$ cells underwent self-renewing divisions in ED 12.75 to 13 5 developing mouse liver.

Example 5

In Vivo Differentiation and Tissue Reconstitution Potential of Clonally Expanding H-CFU-C To determine whether clonally expanding H-CFU-C in culture could generate both hepatocytes and cholangiocytes in viva following transplantation, we injected them into the spleen of mice subjected to severe hepatic disruption by carbon tetrachloride treatment. To distinguish donor cells from recipient cells, the implanted H-CFU-C had been marked genetically with enhanced green fluorescent protein (EGFP) by retrovirus infection.

Retrovirus infection was conducted as follows: a retroviral vector pGCsapEGFP (MSCV) and the virus producing cell line PG13/GCsapEGFP (MSCV) are described elsewhere (Kaneko, S., M. Onodera, Y. Fujiki. T. Nagasawa, and H. Nakauchi. 2001. The simplified retroviral vector GCsap with murine stem cell virus long terminal repeat allows high and continued expression of enhanced green fluorescent protein by human hematopoietic progenitors engrafted in non-obese diabetic/severe combined immunodeficiency mice. Hum. Gene . Ther. 12: 35–44). To increase the viral titer and widen the host range of infection, the supernatant of PG13/GCsapEGFP (MSCV) clones was used to infect the packaging cell line 293 gpg, which expresses the vesicular stomatitis virus G (VSV-G) protein under the tetracycline inducible system (tet off system) (Ory et al., 1996). EGFP-expressing 293 gpg cells were sorted by FACS-Vantage and expanded for subsequent experiments For the collection of VSV-G pseudotype virus, 293 gpg/GCsapEGFP (MSCV) cells were maintained in tetracycline-free medium for 48 to 60 hours prior to harvest. The harvested supernatant was centrifuged at 6000×g for 16 hours at 4° C. to concentrate the virus. The virus pellet was finally resuspended in STEM PRO-34 SFM (Gibco BRL) and stored at −80° C. until used. The estimated titer of the concentrated retrovirus was $1 \times 10^7$ EGFP expressing cells/ml on HeLa cells. For marking of H-CFU-C with EGFP, 25 µl of the concentrated virus supernatant was added to cultures in which cells had grown up to 40–50% confluence in 2.5 ml of standard medium with 5 µg/ml protamine sulfate (Sigma) followed by "spinoculation" (Kotani , H., P. B. 3rd. Newton. S. Zhang, Y. L. Chiang, E. Otto, L. Weaver, R. M. Blaese, W. F. Anderson, and G. J. McGarrity. 1994. Improved methods of retroviral vector transduction and production for gene therapy. Hum. Gene Ther. 5: 19–28). Residual virus was excluded by washing the cells with PBS and changing the medium after 24hours. Frequency of EGFP-positive cells was assayed by FACS-Vantage.

Cell Transplantation was conducted as follows: after the initiation of culture, we maintained H-CFU-C in culture by replating them every 7 days. Donor cells were usually prepared from cells obtained at these passage points; both H-CFU-C and their progeny were administered. We trypsinized, washed , and resuspended $2 \times 10^6$ GFP-tagged H-CFU-C in standard medium (100 µl). They were then injected intrasplenicelly into recipient mice (Balb/cA, 4 weeks old; n=5) (CLEA) under anesthesia. We also injected standard medium without cells as a negative control (n=5). For pre-transplant conditioning of recipient mice, we induced acute liver damage by subcutaneous Injection of 2 ml/kg carbon tetrachloride dissolved in olive oil. Two days afterward, cell transplantation was conducted. Same number of H-CFU-C-derived EGFP transgenic mice was injected intrasplenically into recipient mice (CS7BL/6, 4 weeks old; n=5) (CLEA) following carbon tetrachloride or 4, 4'-methylene dianiline (4, 4'-diaminodiphenylmethane, DAPM) (80–120 mg/kg) (Wako) treatment for hepatocyte or bile duct disruption (Kanz, M. F., L. Kaphalia, B. S. Kaphalia, E. Romagnoli, and G. A. Ansari. 1992. Methylene dianiline: acute toxicity and effects on biliary function. Toxicol. Appl. Pharmacol. 117: 88–97). They were also injected into pancreas (n=4) through common bile duct, and into wall of duodenum (n=5).

Immunohistochemistry was conducted as follows: recipient liver, pancreas, and duodenum were fixed in 4% phosphate-buffered paraformaldehyde overnight at 4° C. and embedded in O.C.T. compound. Cryostat sections of the liver were stained with rabbit anti-albumin (Biogenisis, Poole, UK) as the primary antibody and Cy3-conjugated goat anti-rabbit IgG (Jackson ImmunoResearch Laboratories, West Grove, Pa.) as the secondary antibody. Sections of pancreas were stained with rabbit anti-amylase (Sigma) and Cy3-conjugated goat anti-rabbit IgG. Stained tissues were viewed by using a Zeiss LSM510 laser scanning microscope. For analysis of cholangiocyte differentiation, spleens from recipient animals were fixed in 10% phosphate-buffered formalin, dehydrated in ethanol and xylene, and embedded in paraffin wax at 58–60° C. After de-paraffinization and re-hydration of sections, they were stained with rabbit anti-keratin antibody (Dako, Carpinteria, Calif.) and colorized (LSAB-2kit : Dako) according to manufacturer's instructions.

The concentrated VSV pseudo-typed retrovirus allowed high transduction frequencies, and more than 95% of cells highly expressed EGFP after a single round of infection.

At 38 days post-transplant, in all five recipient mice, donor cells engrafted more efficiently in periportal regions and diffused along hepatic cords (FIG. 5 A). Serial sections stained for albumin showed that many, but not all, donor cells had given rise to hepatocytes (FIG. 5 B). In spleens, many bile duct-like structures composed of cholangiocytes expressing bile duct-specific cytokeratins (Pinkus, G. S., E. M. O'Connor, C. L. Etheridge, and J. M Corson. 1985. Optimal immunoreactivity of keratin proteins in formalin-fixed, paraffin-embedded tissue requires preliminary trypsinization. An immunoperoxidase study of various tumours using polyclonal and monoclonal antibodies. Histochem. Cytochem. 33: 465–473) and containing abundant mucin granules adjoining the luminal space were found (FIGS. 5 C–D). Engraftment was confirmed even 6 months after transplantation.

Since a common cell of origin has been proposed for primitive epithelial cells isolated from liver and pancreas (Rao et al., 1989; Bisgaard, H. C., and S. S. Thorgeirsson. 1991. Evidence for a common cell of origin for primitive epithelial cells isolated from rat liver and pancreas. J. Cell Physiol. 147: 333–343; Chen et al., 1995; Zulewski et al., 2001; Deutsch, G., J. Jung, M. Zheng, J. Lora, and K. S. Zaret. 2001. A bipotential precursor population for pancreas and liver within the embryonic endoderm. Development 128: 871–881), the developmental potential of H-CFU-C was further investigated by RT-PCR analysis and by transplanting them into pancreatic and intestinal environments. We Isolated and propagated H-CFU-C clones from fetal livers (ED 13.5) of EGFP transgenic mice (Okabe et al., 1997). The expression of pancreatic endocrine [β cell: preproinsulin I , preproinsulin II, and IAPP; α cell: preproglucagon; δ cell: preprosomatostatin] and exocrine lineage markers [amylase-2 and HS-lipase] became detectable in the progenies of H-CPU-C (FIG. 5 E). Furthermore, the expression of intestinal [fabp-2 and secretin] and gastric markers (pepsinogen F) was also detected (FIG. 5 E).

Two clones were randomly selected and the cells were transplanted into liver, pancreas, and intestine. As expected, cells of both clones differentiated into hepatocytes or cholangiocytes in recipient livers following regenerative induction by either carbon tetrachloride for hepatocytes, or DAPM for bile duct epithelial cells (FIGS. 5 F–G). Surprisingly, when those cells were injected into pancreas, they integrated into and formed pancreatic ducts (FIGS. 5 H–I) and acinar cells (FIGS. 5 J–L) at 4 months post transplant. Furthermore, upon injection into duodenal wall, those cells integrated into intestinal epithelium, and some of them differentiated into goblet cells (FIG. 5 M, insets) and reconstituted intestinal villi and crypts (FIG. 5 M).

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications and patent applications mentioned in this specification are indicative of the level of skill of those skilled in the art to which this invention pertains. All publications and patent applications are herein incorporated by reference to the same extent as if each individual publication, or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated cloned, self-renewing pluripotent fetal mouse hepatic stem cell having the cellular marker phenotype of c-Met$^+$ CD49f$^{+/low}$ CD29$^+$ cKit$^-$ CD45$^-$ TER119$^-$.

2. The stem cell according to claim 1, which is capable of differentiating into hepatocytes or cholangiocytes.

3. The stem cell according to claim 1, which is capable of differentiating into pancreatic ductal, acinar, or intestinal epithelial cells.

4. A method for producing cloned, self-renewing pluripotent fetal mouse stem cells, comprising:
providing fetal mouse liver cells;
fractionating said cells by selecting cells having the cellular marker phenotype of c-Met$^+$ CD49f$^{+/low}$ CD29$^+$ cKit$^-$ CD45$^-$ TER119$^-$; and
clonally propagating the selected cells in culture.

* * * * *